(12) United States Patent
Lewis et al.

(10) Patent No.: US 11,801,272 B2
(45) Date of Patent: *Oct. 31, 2023

(54) BACILLUS STRAINS IMPROVING HEALTH AND PERFORMANCE OF PRODUCTION ANIMALS

(71) Applicant: Novozymes A/S, Bagsvaerd (DK)

(72) Inventors: Derrick Lewis, Durham, NC (US); Marianne Thorup Cohn, Copenhagen (DK); Adam Nelson, Salem, VA (US); Preben Nielsen, Horsholm (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/500,606

(22) Filed: Oct. 13, 2021

(65) Prior Publication Data

US 2022/0143110 A1 May 12, 2022

Related U.S. Application Data

(63) Continuation of application No. 15/542,161, filed as application No. PCT/US2016/014524 on Jan. 22, 2016, now Pat. No. 11,166,989.

(60) Provisional application No. 62/260,882, filed on Nov. 30, 2015, provisional application No. 62/106,892, filed on Jan. 23, 2015.

(51) Int. Cl.
| | | |
|---|---|---|
| *A61K 35/742* | (2015.01) | |
| *C12N 1/20* | (2006.01) | |
| *A23K 10/18* | (2016.01) | |
| *A23K 50/75* | (2016.01) | |
| *A61P 31/04* | (2006.01) | |
| *C12R 1/07* | (2006.01) | |

(52) U.S. Cl.
CPC ............ *A61K 35/742* (2013.01); *A23K 10/18* (2016.05); *A23K 50/75* (2016.05); *A61P 31/04* (2018.01); *C12N 1/20* (2013.01); *C12N 1/205* (2021.05); *C12R 2001/07* (2021.05)

(58) Field of Classification Search
CPC ...... A61K 35/742; A23K 50/75; A23K 10/18; A61P 31/04; C12N 1/205; C12N 1/20; C12R 2001/07
USPC .......................................................... 435/61
See application file for complete search history.

(56) References Cited

U.S. PATENT DOCUMENTS

| | | | |
|---|---|---|---|
| 4,919,936 | A | 4/1990 | Iwanami |
| 5,733,355 | A | 3/1998 | Hibino |
| 8,540,981 | B1 | 9/2013 | Wehnes |
| 8,906,668 | B2 | 12/2014 | Henn et al. |
| 11,166,989 | B2 | 11/2021 | Lewis et al. |
| 11,331,351 | B2 | 5/2022 | Lewis et al. |

| | | | |
|---|---|---|---|
| 2004/0101525 | A1 | 5/2004 | Lin |
| 2009/0280090 | A1 | 11/2009 | Rehberger |
| 2009/0318292 | A1 | 12/2009 | Kong |
| 2010/0092428 | A1* | 4/2010 | Schmidt .................. A61P 3/00 426/2 |
| 2011/0318289 | A1 | 12/2011 | Frodyma |
| 2013/0136695 | A1 | 5/2013 | Hargis |
| 2013/0330307 | A1 | 12/2013 | Millan |
| 2014/0037582 | A1 | 2/2014 | Romero |
| 2014/0234279 | A1 | 8/2014 | Millan |
| 2016/0051599 | A1 | 2/2016 | Drahos et al. |

FOREIGN PATENT DOCUMENTS

| | | |
|---|---|---|
| CN | 103882097 | 6/2014 |
| WO | 2007/064741 A2 | 6/2007 |
| WO | 2010/033714 A1 | 3/2010 |
| WO | 2012/009712 A2 | 1/2012 |
| WO | 2012/105805 A2 | 9/2012 |
| WO | 2013/029013 A1 | 2/2013 |
| WO | 2013/096369 A1 | 6/2013 |
| WO | 2013/153159 A1 | 10/2013 |
| WO | 2014/169046 A1 | 10/2014 |

OTHER PUBLICATIONS

Anonymous, EFSA Journal, vol. 8, No. 3, article 1552, pp. 1-7 (2010).
Anonymous, EFSA Journal, vol. 10, No. 1, article 2536, pp. 1-19 (2012).
Anonymous, EFSA Supporting Publication, article EN-587, pp. 1-13 (2014).
Essghaier et al., Journal of Applied Microbiology, vol. 106, No. 3, pp. 833-846 (2009).
Gang et al., Biomed. Environ. Sci., vol. 28, No. 8, pp. 620-625 (2015).
Jayaraman et al., Poultry Science, vol. 92, No. 2, pp. 370-374 (2013).
Knap et al., Avian Diseases, vol. 54, No. 2, pp. 931-935 (2010).
Maruta et al., Anim. Sci. Technol. (Jpn.), vol. 67, No. 5, pp. 403-409 (1996).
Prieto et al., Marine Drugs, vol. 12, No. 5, pp. 2422-2445 (2014).
Sathishkumar et al., Kemin Animal Nutrition and Health, "Influence of CLOSTAT on Production Performance of Commercial Layers (BV 300)" (2013).
Tactacan et al., J. Appl. Poult. Res., vol. 22, No. 4, pp. 825-831 (2013).
Teo et al., J. Appl. Poult. Res., vol. 15, No. 2, pp. 229-235 (2006).
Paineau et al., FEMS Immunol. Med. Microbiol., vol. 53, pp. 107-113 (2008).

(Continued)

*Primary Examiner* — Jennifer M. H. Tichy

(74) *Attorney, Agent, or Firm* — Adam Rucker

(57) ABSTRACT

The present invention relates to *Bacillus* strains which improves health and performance of production animals. The invention further relates to compositions comprising the *Bacillus* strains.

20 Claims, 3 Drawing Sheets

Specification includes a Sequence Listing.

(56) References Cited

OTHER PUBLICATIONS

Zeigler, UniProtKB Accession No. E0TXL5 (2010).
Anastassiadou et al., European Food Safety Authority, EFSA Journal, 2021, vol. 19, (1) 6381, pp. 1-20.
Bampidis et al., 2022, EFSA Journal, vol. 20, (4) 7244, pp. 1-8.
Källqvist et al., VKM Report, 2016, 21.
Pandin et al., J Biotechnol, 2018, vol. 278, pp. 10-19.
Rowe(ed) et al., Handbook of Pharmaceutical Excipients 6th Ed, 2009, pp. 185-188.

* cited by examiner

Alignment of 16 S rDNA sequences

SEQ ID NO: 1 (DSM 29869), SEQ ID NO: 2 (DSM 29870), SEQ ID NO: 3 (DSM 29871),
SEQ ID NO: 4 (DSM 29872), SEQ ID NO: 5 (*Bacillus vallismortis* AB021198), SEQ ID NO: 6
(*Bacillus subtilis* from AJ276351), and SEQ ID NO: 7 (*Bacillus amyloliquefaciens* AB255669)

| | | |
|---|---|---|
| AJ276351 B subtilis | GGCTACACACGTGCTACAATGGACAGAACAAAGGGCAGCAAGACCGCGAGGTTAAGCCAATCCCACAAATCTGTTCTCAG | 1280 |
| DSM29871 | GGCTACACACGTGCTACAATGGACAGAACAAAGGGCAGCAAGACCGCGAGGTTAAGCCAATCCCACAAATCTGTTCTCAG | 1280 |
| DSM29870 | GGCTACACACGTGCTACAATGGACAGAACAAAGGGCAGCAAGACCGCGAGGTTAAGCCAATCCCACAAATCTGTTCTCAG | 1280 |
| AB021198 B vallismortis | GGCTACACACGTGCTACAATGGACAGAACAAAGGGCAGCGAAGCCGCGAGGTTAAGCCAATCCCACAAATCTGTTCTCAG | 1280 |
| AB255669 B amyloliquefaciens | GGCTACACACGTGCTACAATGGACAGAACAAAGGGCAGCGAAACCGCGAGGTTAAGCCAATCCCACAAATCTGTTCTCAG | 1280 |
| DSM29869 | GGCTACACACGTGCTACAATGGACAGAACAAAGGGCAGCGAACCCGCGAGGTTAAGCCAATCCCACAAATCTGTTCTCAG | 1280 |
| DSM29872 | GGCTACACACGTGCTACAATGGACAGAACAAAGGGCAGCGAAGCCGCGAGGTTAAGCCAATCCCACAAATCTGTTCTCAG | 1280 |

| | | |
|---|---|---|
| AJ276351 B subtilis | TTCGGATCCGCAGTCTGCAACTCGACTGCGTGAAGCTGGAATCGCTAGTAATCGCGGATCAGCATGCCGCGGTGAATACGT | 1360 |
| DSM29871 | TTCGGATCCGCAGTCTGCAACTCGACTGCGTGAAGCTGGAATCGCTAGTAATCGCGGATCAGCATGCCGCGGTGAATACGT | 1360 |
| DSM29870 | TTCGGATCCGCAGTCTGCAACTCGACTGCGTGAAGCTGGAATCGCTAGTAATCGCGGATCAGCATGCCGCGGTGAATACGT | 1360 |
| AB021198 B vallismortis | TTCGGATCCGCAGTCTGCAACTCGACTGCGTGAAGCTGGAATCGCTAGTAATCGCGGATCAGCATGCCGCGGTGAATACGT | 1360 |
| AB255669 B amyloliquefaciens | TTCGGATCCGCAGTCTGCAACTCGACTGCGTGAAGCTGGAATCGCTAGTAATCGCGGATCAGCATGCCGCGGTGAATACGT | 1360 |
| DSM29869 | TTCGGATCCGCAGTCTGCAACTCGACTGCGTGAAGCTGGAATCGCTAGTAATCGCGGATCAGCATGCCGCGGTGAATACGT | 1360 |
| DSM29872 | TTCGGATCCGCAGTCTGCAACTCGACTGCGTGAAGCTGGAATCGCTAGTAATCGCGGATCAGCATGCCGCGGTGAATACGT | 1360 |

| | | |
|---|---|---|
| AJ276351 B subtilis | TCCCGGGCCTTGTACACACCGCCCGTCACACCACGAGAGTTTGTAACACCCGAAGTCGGTGAGGTAACCTTTTAGGAGCC | 1440 |
| DSM29871 | TCCCGGGCCTTGTACACACCGCCCGTCACACCACGAGAGTTTGTAACACCCGAAGTCGGTGAGGTAACCTTTTAGGAGCC | 1440 |
| DSM29870 | TCCCGGGCCTTGTACACACCGCCCGTCACACCACGAGAGTTTGTAACACCCGAAGTCGGTGAGGTAACCTTTTAGGAGCC | 1440 |
| AB021198 B vallismortis | TCCCGGGCCTTGTACACACCGCCCGTCACACCACGAGAGTTTGTAACACCCGAAGTCGGTGAGGTAACCTTTTAGGAGCC | 1440 |
| AB255669 B amyloliquefaciens | TCCCGGGCCTTGTACACACCGCCCGTCACACCACGAGAGTTTGTAACACCCGAAGTCGGTGAGGTAACCTTTTAGGAGCC | 1440 |
| DSM29869 | TCCCGGGCCTTGTACACACCGCCCGTCACACCACGAGAGTTTGTAACACCCGAAGTCGGTGAGGTAACCTTTAGAGCC | 1440 |
| DSM29872 | TCCCGGGCCTTGTACACACCGCCCGTCACACCACGAGAGTTTGTAACACCCGAAGTCGGTGAGGTAACCTTTAGGAGCC | 1440 |

BACILLUS STRAINS IMPROVING HEALTH AND PERFORMANCE OF PRODUCTION ANIMALS

CROSS-REFERENCE TO RELATED APPLICATIONS

This application is a continuation of U.S. patent application Ser. No. 15/542,161, filed on Jul. 7, 2017 and published on Mar. 28, 2019 as US2019/0091269, which application is a 35 U.S.C. 371 national application of international application no. PCT/US2016/014524 filed Jan. 22, 2016 and published on Jul. 28, 2016 as WO2016/118864, which claims priority or the benefit under 35 U.S.C. 119 of U.S. application Nos. 62/106,892 and 62/260,882 filed Jan. 23, 2015 and Nov. 30, 2015, respectively. The content of each application is fully incorporated herein by reference.

REFERENCE TO A DEPOSIT OF BIOLOGICAL MATERIAL

This application contains a reference to a deposit of biological material, which deposit is incorporated herein by reference.

REFERENCE TO SEQUENCE LISTING

This application contains a Sequence Listing in computer readable form. The computer readable form is incorporated herein by reference.

Index to sequence listing:
SEQ ID NO: 1 is 16S rDNA of DSM 29869.
SEQ ID NO: 2 is 16S rDNA of DSM 29870.
SEQ ID NO: 3 is 16S rDNA of DSM 29871.
SEQ ID NO: 4 is 16S rDNA of DSM 29872.
SEQ ID NO: 5 is 16S rDNA of *Bacillus vallismortis* from AB021198.
SEQ ID NO: 6 is 16S rDNA of *Bacillus subtilis* from AJ276351.
SEQ ID NO: 7 is 16S rDNA of *Bacillus amyloliquefaciens* from AB255669.
SEQ ID NO: 8 to SEQ ID NO: 13: PCR and sequencing primers.

BACKGROUND OF THE INVENTION

Field of the Invention

The present invention relates to *Bacillus* strains which improves the health and performance of production animals. The invention further relates to compositions comprising the *Bacillus* strains.

Background of the Invention

*Clostridium perfringens* (*C. perfringens*) is a Gram-positive, rod-shaped, anaerobic, spore-forming bacterium of the genus *Clostridium*. *C. perfringens* is widely present in nature and can be found as a component of decaying vegetation, marine sediment, the intestinal tract of humans and other vertebrates, insects, and soil.

Infections due to *C. perfringens* show evidence of tissue necrosis, bacteremia, emphysematous cholecystitis, and gas gangrene, which is also known as clostridial myonecrosis. *C. perfringens* can also result in polymicrobial anaerobic infections.

The incidence of *Clostridium perfringens*-associated necrotic enteritis in poultry has increased in countries that stopped using antibiotic growth promoters. Necrotic enteritis is an enterotoxemic disease that results in significant economic losses in the poultry industry.

There is a need to develop tools and strategies for the prevention and control of *C. perfringens* in mono-gastric animals such as poultry. Whilst the vaccination of animals has been suggested, there are challenges associated with vaccinating thousands of animals. Thus discovering a solution which could be administered as an additive in an animal feed would be advantageous.

It is thus an object of the invention to provide solutions which prevents and/or controls *C. perfringens* in mono-gastric animals such as poultry by use of an animal feed comprising one or more bacteria with activity against *Clostridium perfringens*.

A further object of the invention is to provide a solution that does not present a risk for the health of the animal. The solution to this problem is use of non-hemolytic *Bacillus* strains with activity against *Clostridium perfringens*.

A challenge of delivering *Bacillus* spp. in feed is the common use of antibiotics as growth promoters in feed. Therefore it is necessary to determine the compatibility of strains with commonly-used feed antibiotics such as monensin in order to identify any potential conflicts with use as a direct fed microbial. The present invention relates in one embodiment to a *Bacillus* strains with high compatibility with monensin.

DESCRIPTION OF THE RELATED ART

Knap et al. (2010) describes that *Bacillus licheniformis* has an effect on necrotic enteritis in broiler chickens (Knap, Lund, Kehlet, Hofacre, and Mathis; *Bacillus licheniformis* Prevents Necrotic Enteritis in Broiler Chickens; Avian Diseases 54(2):931-935. 2010). This *Bacillus licheniformis* strain has no effect on *Clostridium perfringens* in vitro as demonstrated in Example 2.

Clostat (alias *Bacillus* PB6) is described in WO2007/064741. *Bacillus* PB6 has antagonistic effect against *C. perfringens*. *Bacillus* PB6 is hemolytic as described in Example 1.

SUMMARY OF THE INVENTION

It has been surprisingly found that the addition of direct fed microbes (DFM) from *Bacillus* species to animal feed can be used to prevent and/or control *C. perfringens* infections and/or necrotic enteritis in mono-gastric animal such as pigs and/or poultry. The *Bacillus* species can also improve the body weight gain and/or feed conversion rate (e.g., in both *Clostridium perfringens* challenged and unchallenged chickens).

In a first aspect the invention relates to a *Bacillus* strain characterized in that:
  i) the *Bacillus* strain is non-hemolytic,
  ii) the *Bacillus* strain has antimicrobial activity against *Clostridium perfringens* and
  iii) the *Bacillus* strain improves body weight gain and/or feed conversion rate in chickens fed with the *Bacillus* strain.

In a second aspect the invention relates to a *Bacillus* strain characterized in that:
  i) the *Bacillus* strain is non-hemolytic,
  ii) the *Bacillus* strain has antimicrobial activity against *Clostridium perfringens* and iii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline.

In a third aspect the invention relates to a *Bacillus* strain characterized in that:
  i) the *Bacillus* strain is non-hemolytic,
  ii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline and
  iii) the *Bacillus* strain improves body weight gain and/or feed conversion rate in chickens fed with the *Bacillus* strain.

In a fourth aspect the invention relates to a *Bacillus* strain characterized in that:
  i) the *Bacillus* strain is non-hemolytic,
  ii) the *Bacillus* strain has antimicrobial activity against *Clostridium perfringens* and optionally
  iii) the *Bacillus* strain has enzymatic activity under aerobic and/or anaerobic conditions that hydrolyzes one or more of the substrates selected from the group consisting of Amylose, Arabinan, Arabinoxylan, Casein and Xylan.

The invention further relates to the strain having the deposit accession number DSM 29869; a strain having all of the identifying characteristics of *Bacillus* DSM 29869 or a mutant thereof.

The invention further relates to the strain having the deposit accession number DSM 29870; a strain having all of the identifying characteristics of *Bacillus* DSM 29870 or a mutant thereof.

The invention further relates to the strain having the deposit accession number DSM 29871; a strain having all of the identifying characteristics of *Bacillus* DSM 29871 or a mutant thereof.

The invention further relates to the strain having the deposit accession number DSM 29872; and a strain having all of the identifying characteristics of *Bacillus* DSM 29872 or a mutant thereof.

The present invention also relates to compositions comprising one or more of the *Bacillus* strains according to the invention which improves health and performance of production animals.

In a preferred embodiment the invention relates to a composition, e.g., comprising a carrier and a *Bacillus* strain wherein:
  i. the *Bacillus* strain is selected from the group consisting of:
    the strain having the deposit accession number DSM 29869; a strain having all of the identifying characteristics of *Bacillus* DSM 29869 or a mutant thereof,
    the strain having the deposit accession number DSM 29870; a strain having all of the identifying characteristics of *Bacillus* DSM 29870 or a mutant thereof,
    the strain having the deposit accession number DSM 29871; a strain having all of the identifying characteristics of *Bacillus* DSM 29871 or a mutant thereof,
    the strain having the deposit accession number DSM 29872; and a strain having all of the identifying characteristics of *Bacillus* DSM 29872 or a mutant thereof, and
  ii. the *Bacillus* strain has antimicrobial activity against *Clostridium perfringens* (such as *Clostridium perfringens* strains 23 or 48 [Gholamiandekhordi A R, Ducatelle R, Heyndrickx M, Haesebrouck F, Van Immerseel F. 2006. Molecular and phenotypical characterization of *Clostridium perfringens* isolates from poultry flocks with different diseasestatus. Vet. Microbiol. 113:143-152] and/or *E. coli* (such as ATCC10536 or ATCC25922).

In a preferred embodiment the *Bacillus* strain has a high compatibility with monensin such as being compatible with at least 2.4 µg/ml monensin as determined in Example 12.

BRIEF DESCRIPTION OF DRAWINGS

FIGS. 1A, 1B and 1C. Alignment of 16 S rDNA sequences. SEQ ID NO: 1 (DSM 29869), SEQ ID NO: 2 (DSM 29870), SEQ ID NO: 3 (DSM 29871), SEQ ID NO: 4 (DSM 29872), SEQ ID NO: 5 (*Bacillus vallismortis* AB021198), SEQ ID NO: 6 (*Bacillus subtilis* from AJ276351), and SEQ ID NO: 7 (*Bacillus amyloliquefaciens* AB255669) have been aligned. The region covering position 481-1200 is not shown in FIG. 1B (in this region all sequences are identical).

DEFINITIONS

Figure 1B:
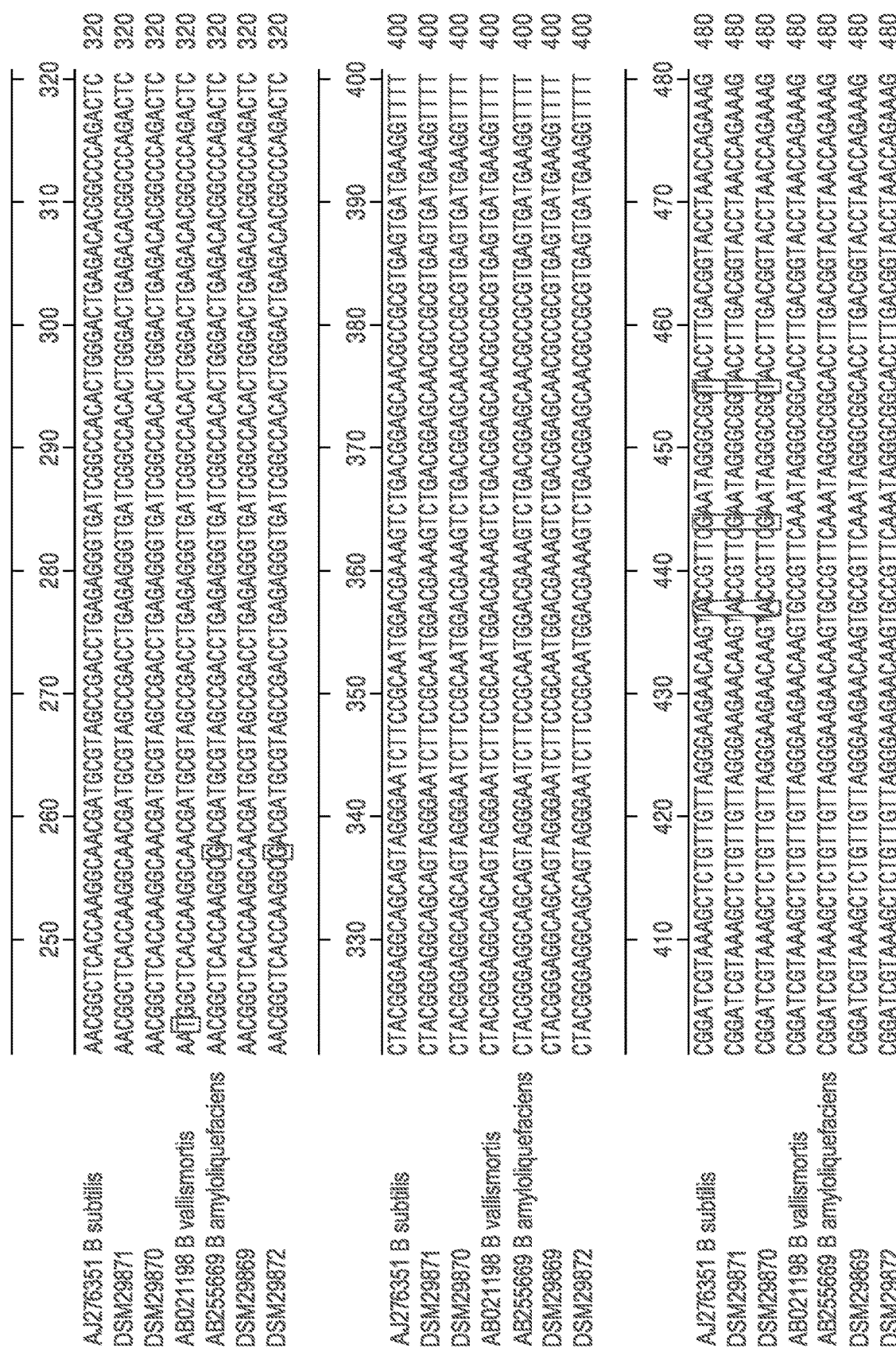

In general, the terms and phrases used herein have their art-recognized meaning, which can be found by reference to standard texts, journal references, and context known to those skilled in the art. The following definitions are provided to clarify their specific use in context of the disclosure.

As used herein, the singular forms "a", "an" and "the" are intended to include the plural forms as well, unless the context clearly indicates otherwise.

Antimicrobial activity against *Clostridium perfringens*: The term "Antimicrobial activity against *Clostridium perfringens*" means that the growth of *Clostridium perfringens* is inhibited and/or that some or all of the *Clostridium perfringens* are killed. This can be determined by the assay described in Example 2.

Body Weight Gain: The Body Weight Gain of an animal is the increase of body weight of the animal over a specified time period. An example of Body Weight Gain determination is given in Example 8.

Composition: The term "composition" refers to a composition comprising a carrier and at least one bacterial strain as described herein. The compositions described herein may be mixed with an animal feed(s) and referred to as a "mash feed."

Control *C. perfringens* infections and/or necrotic enteritis: The term "control *C. perfringens* infections and/or necrotic enteritis" means a method and/or composition that partly or completely inhibits *C. perfringens* infections and/or necrotic enteritis in an animal. Accordingly, the term "control *C. perfringens* infections and/or necrotic enteritis" means the *C. perfringens* infections and/or the necrotic enteritis is reduced or completely eliminated or prevented.

Direct Fed Microbial: The term "direct fed microbial" means live micro-organisms including spores which, when administered in adequate amounts, confer a benefit, such as improved digestion or health, on the host.

Enzymatic activity under aerobic conditions: The term "enzymatic activity under aerobic conditions" means activity of enzymes produced by a *Bacillus* strain during growth under aerobic conditions as described in Example 6.

Enzymatic activity under anaerobic conditions: The term "enzymatic activity under anaerobic conditions" means activity of enzymes produced by a *Bacillus* strain during growth under anaerobic conditions as described in Example 6.

European Production Efficacy Factor (EPEF): The European Production Efficacy Factor is a way of comparing the live-bird performance of flocks. This single-figure facilitates comparison of performance within and among farms and can be used to assess environmental, climatic and managerial variables. The EPEF is calculated as [(liveability (%)× Liveweight (kg))/(Age at depletion (days)×FCR)]×100, wherein livability is the percentage of birds alive at slaughter, Liveweight is the average weight of the birds at slaughter, age of depletion is the age of the birds at slaughter and FCR is the feed conversion ratio at slaughter.

Fed: The term "fed" means any type of oral administration such as administration via an animal feed or via drinking water.

FCR (Feed Conversion Rate): FCR is a measure of an animal's efficiency in converting feed mass into increases of the desired output. Animals raised for meat—such as swine, poultry and fish—the output is the mass gained by the animal. Specifically FCR is the mass of the food eaten divided by the output, all over a specified period. FCR can be determined as described in Example 8. Improvement in FCR means reduction of the FCR value. A FCR improvement of 2% means that the FCR was reduced by 2%.

Isolated: The term "isolated" means that the one or more bacterial strains described herein are in a form or environment which does not occur in nature, that is, the one or more bacterial strains are at least partially removed from one or more or all of the naturally occurring constituents with which it is associated in nature.

Non-hemolytic: Hemolysis is the breakdown of red blood cells. The ability of bacterial colonies to induce hemolysis when grown on blood agar is used to classify bacterial strains into hemolytic and non-hemolytic strains. In this context hemolysis is defined as described in EFSA Journal 2011; 9(11):2445, using *Bacillus subtilis* 168 (BGSC-1A1, *Bacillus* Genetic Stock Center) as a negative control. A *Bacillus* strain can be classified as non-hemolytic using the assay described in Example 1.

Poultry: The term "poultry" means domesticated birds kept by humans for the eggs they produce and/or their meat and/or their feathers. Poultry includes broilers and layers. Poultry include members of the superorder Galloanserae (fowl), especially the order Galliformes (which includes chickens, Guineafowls, quails and turkeys) and the family Anatidae, in order Anseriformes, commonly known as "waterfowl" and including domestic ducks and domestic geese. Poultry also includes other birds that are killed for their meat, such as the young of pigeons. Examples of poultry include chickens (including layers, broilers and chicks), ducks, geese, pigeons, turkeys and quail.

Prevent *C. perfringens* infections and/or necrotic enteritis: The term "prevent *C. perfringens* infections and/or necrotic enteritis" means a method and/or composition that prevents development of a *C. perfringens* infection and/or necrotic enteritis in an animal.

Sensitive to antibiotics: The term "sensitive to antibiotics" means the phenotypic property of a bacterial strain, that growth of said bacterial strain is inhibited under conditions where the bacterial strain would otherwise grow. In this context sensitivity to antibiotics is tested after the CLSI guidelines (M07-A9 Methods for Dilution Antimicrobial Susceptibility Tests for Bacteria That Grow Aerobically; 2012). The *S. aureus* ATCC 29213 is used as reference strain, which means that it should be included in the test, and that the results are only valid if *S. aureus* ATCC 29213 show results in compliance with the breakpoints of the CLSI guideline (see Example 5 Table 5.5) (M100-S24 Performance Standards for Antimicrobial Susceptibility Testing; informational Supplement, 2014). A strain of *Bacillus* is considered sensitive if the growth is detected at or below the breakpoint concentration of the appropriate antibiotic specified in EFSA journal 2012; 10(6):2740.

Spore: The terms "spore" and "endospore" are interchangeable and have their normal meaning which is well known and understood by those of skill in the art. As used herein, the term spore refers to a microorganism in its dormant, protected state.

Stable: The term "stable" is a term that is known in the art, and in a preferred aspect, stable is intended to mean the ability of the microorganism to remain in a spore form until it is administered to an animal to improve the health of the animal.

Swine: The term "swine" or "pigs" means domesticated pigs kept by humans for food, such as their meat. Swine includes members of the genus *Sus*, such as *Sus scrofa domesticus* or *Sus domesticus* and include piglets, growing pigs, and sows.

DETAILED DESCRIPTION OF THE INVENTION

It has been surprisingly found that the addition of direct fed microbes (DFM) from *Bacillus* species to animal feed can be used to prevent and/or control *C. perfringens* infections and/or necrotic enteritis in mono-gastric animal such as pigs and/or poultry and at the same time improve the body weight gain and/or feed conversion rate (in both *Clostridium perfringens* challenged and unchallenged chickens).

*Bacillus* Strains of the Invention

The invention relates to the following aspects with respect to *Bacillus* strains:

Aspect 1: A *Bacillus* strain characterized in that:
  i) the *Bacillus* strain is non-hemolytic,
  ii) the *Bacillus* strain has antimicrobial activity against *Clostridium perfringens* and
  iii) the *Bacillus* strain improves body weight gain and/or feed conversion rate in chickens fed with the *Bacillus* strain.

Aspect 2: A *Bacillus* strain characterized in that:
  i) the *Bacillus* strain is non-hemolytic,
  ii) the *Bacillus* strain has antimicrobial activity against *Clostridium perfringens* and
  iii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline.

Aspect 3: A *Bacillus* strain characterized in that:
  i) the *Bacillus* strain is non-hemolytic,
  ii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline and
  iii) the *Bacillus* strain improves body weight gain and/or feed conversion rate in chickens fed with the *Bacillus* strain.

Aspect 4: A *Bacillus* strain characterized in that:
  i) the *Bacillus* strain is non-hemolytic,
  ii) the *Bacillus* strain has antimicrobial activity against *Clostridium perfringens* and optionally iii) the *Bacillus* strain has enzymatic activity under aerobic and/or anaerobic conditions that hydrolyzes one or more of the substrates selected from the group consisting of Amylose, Arabinan, Arabinoxylan, Casein and Xylan.

In a preferred embodiment the *Bacillus* according to Aspect 1, 2 3 or 4 has a high compatibility with monensin such as being compatible with at least 2.3 µg/ml monensin as determined in Example 12. It is even more preferred that the *Bacillus* strain is compatible with at least 2.4 µg/ml monensin as determined in Example 12 (such as at least 2.5 µg/ml monensin as determined in Example 12, such as at least 2.6 µg/ml monensin as determined in Example 12 or such as at least 2.7 µg/ml monensin as determined in Example 12).

Sensitivity to Vancomycin, Clindamycin, Chloramphenicol, Gentamicin, Kanamycin, Streptomycin, Erythromycin and Tetracycline can, e.g., be determined as described in Example 5.

Enzymatic activity under aerobic and/or anaerobic conditions that hydrolyzes one or more of the substrates selected from the group consisting of Amylose, Arabinan, Arabinoxylan, Casein and Xylan can, e.g., be determined as described in Example 6.

In one embodiment the *Bacillus* strain according to Aspect 1, 2 or 3 has enzymatic activity under aerobic and/or anaerobic conditions that hydrolyzes one or more of the substrates selected from the group consisting of Amylose, Arabinan, Arabinoxylan, Casein and Xylan.

In one embodiment the *Bacillus* strain according to Aspect 2, 3 or 4 improves one or more performance parameters in poultry selected from the list consisting of body weight gain, European Production Efficacy Factor and feed conversion rate in chickens fed with the *Bacillus* strain.

In one embodiment, the *Bacillus* strain according to Aspect 3 has antimicrobial activity against *Clostridium perfringens*. Antimicrobial activity against *Clostridium perfringens* can, e.g., be determined as described in Example 2.

In one embodiment the *Bacillus* strain according to Aspect 1 or 4 is sensitive to at least seven such as eight of the antibiotics selected from the group consisting of Vancomycin, Clindamycin, Chloramphenicol, Gentamicin, Kanamycin, Streptomycin, Erythromycin and Tetracycline.

In one embodiment the improvement of feed conversion rate (FCR) for Aspect 1, 2, 3 or 4 results in a FCR of −2.5% or less than −2.5%, such as less than −2.6%, such as less than −2.7%, such as less than −2.8%, such less than −2.9%, such as less than −3.0%. In a preferred embodiment the improvement of FCR results in a FCR of from −5% to −2% such as a FCR from −4% to −2%, such as a FCR of from −3.5% to −2.5%. In a specific embodiment the improvement of FCR for Aspect 1, 2, 3 or 4 results in a FCR within an interval selected from the group consisting of from −5% to −4.5%, from −4.5% to −4%, from −4% to −3.8%, from −3.8% to −3.6%, from −3.6% to −3.4%, from −3.4% to −3.2%, from −3.2 to −3.0%, from −3.0% to −2.8% and from −2.8 to −2.5%, or any combination of these intervals. The FCR can be determined as described in Example 8.

In one embodiment the improvement in body weight gain for Aspect 1, 2, 3 or 4 results in a body weight gain of at least 0.5%, such as at least 0.8%, such as at least 1.5%, such as at least 1.8%, such as at least 2.0%, such as at least 2.3%, such as at least 3.5%, such as at least 4.2%, such as at least 5.2%, such as at least 6.5%, such as at least 7.3%. In a preferred embodiment the improvement in body weight gain for Aspect 1, 2, 3 or 4 results in a body weight gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof. The body weight gain can be determined as described in Example 8.

In one embodiment the *Bacillus* strain according to Aspect 1, 2, 3 or 4 wherein the *Bacillus* strain comprises 16S rDNA that is more than 98% (such as more than 98.5%, such as more than 99%, such as more than 99.5%, such as more than 99.5%) sequence identity to SEQ ID NO: 1.

In one embodiment the *Bacillus* strain according to Aspect 1, 2, 3 or 4 wherein the *Bacillus* strain comprises 16S rDNA that is more than 98% (such as more than 98.5%, such as more than 99%, such as more than 99.5%) sequence identity to SEQ ID NO: 2.

In one embodiment the *Bacillus* strain according to Aspect 1, 2, 3 or 4 wherein the *Bacillus* strain comprises 16S rDNA that is more than 98% (such as more than 98.5%, such as more than 99%, such as more than 99.5%) sequence identity to SEQ ID NO: 3.

In one embodiment the *Bacillus* strain according to Aspect 1, 2, 3 or 4 wherein the *Bacillus* strain comprises 16S rDNA that is more than 98% (such as more than 98.5%, such as more than 99%, such as more than 99.5%) sequence identity to SEQ ID NO: 4.

In one embodiment the *Bacillus* strain according to Aspect 1, 2, 3 or 4 is a *Bacillus subtilis* strain, a *Bacillus amyloliquefaciens* strain or a *Bacillus licheniformis* strain.

In one embodiment the *Bacillus* strain according to Aspect 1, 2, 3 or 4 has antimicrobial effect against *E. coli*. The effect against *E. coli* can, e.g., be determined as described in Example 4.

In one embodiment the *Bacillus* strain according to Aspect 1, 2, 3 or 4 is the *Bacillus* strain having deposit accession number DSM 29869, or a strain having all of the identifying characteristics of *Bacillus* DSM 29869 or a mutant thereof that has antimicrobial activity against *Clostridium perfringens*. In another embodiment the *Bacillus* strain according to Aspect 1, 2, 3 or 4 is the *Bacillus* strain having deposit accession number DSM 29870, or a strain having all of the identifying characteristics of *Bacillus* DSM 29870 or a mutant thereof that has antimicrobial activity against *Clostridium perfringens*. In yet another embodiment the *Bacillus* strain according to Aspect 1, 2, 3 or 4 is the *Bacillus* strain having deposit accession number DSM 29871, or a strain having all of the identifying characteristics of *Bacillus* DSM 29871 or a mutant thereof that has antimicrobial activity against *Clostridium perfringens*. In a further embodiment the *Bacillus* strain according to Aspect 1, 2, 3 or 4 is the *Bacillus* strain having deposit accession number DSM 29872, or a strain having all of the identifying characteristics of *Bacillus* DSM 29872 or a mutant thereof that has antimicrobial activity against *Clostridium perfringens*.

The invention relates in one embodiment to a *Bacillus* strain having deposit accession number DSM 29869 or a strain having all of the identifying characteristics of *Bacillus* DSM 29869 or a mutant thereof. The invention relates in another embodiment to a *Bacillus* strain having deposit accession number DSM 29870 or a strain having all of the identifying characteristics of *Bacillus* DSM 29870 or a mutant thereof. The invention relates in another embodiment to a *Bacillus* strain having deposit accession number DSM 29871 or a strain having all of the identifying characteristics of *Bacillus* DSM 29871 or a mutant thereof. The invention relates in a further embodiment to a *Bacillus* strain having deposit accession number DSM 29872 or a strain having all of the identifying characteristics of *Bacillus* DSM 29872 or a mutant thereof.

The invention also relates to a biologically pure culture of the *Bacillus* strain according to aspect 1, 2, 3 or 4. In a further embodiment the invention relates to a biologically pure culture of the *Bacillus* strain having deposit accession number DSM 29869 or a strain having all of the identifying characteristics of *Bacillus* DSM 29869 or a mutant thereof. In a further embodiment the invention relates to a biologically pure culture of the *Bacillus* strain having deposit accession number DSM 29870 or a strain having all of the identifying characteristics of *Bacillus* DSM 29870 or a mutant thereof. In a further embodiment the invention relates to a biologically pure culture of the *Bacillus* strain having deposit accession number DSM 29871 or a strain having all of the identifying characteristics of *Bacillus* DSM 29871 or a mutant thereof. In a further embodiment the invention relates to a biologically pure culture of the *Bacillus* strain having deposit accession number DSM 29872 or a strain having all of the identifying characteristics of *Bacillus* DSM 29872 or a mutant thereof.

The invention also relates to an isolated *Bacillus* strain according to aspect 1, 2, 3 or 4. In a further embodiment the invention also relates to an isolated *Bacillus* strain having deposit accession number DSM 29869 or an isolated strain having all of the identifying characteristics of *Bacillus* DSM 29869 or a mutant thereof. In a further embodiment the invention also relates to an isolated *Bacillus* strain having deposit accession number DSM 29870 or an isolated strain having all of the identifying characteristics of *Bacillus* DSM 29870 or a mutant thereof. In a further embodiment the invention also relates to an isolated *Bacillus* strain having deposit accession number DSM 29871 or an isolated strain having all of the identifying characteristics of *Bacillus* DSM 29871 or a mutant thereof. In a further embodiment the invention also relates to an isolated *Bacillus* strain having deposit accession number DSM 29872 or an isolated strain having all of the identifying characteristics of *Bacillus* DSM 29872 or a mutant thereof.

Compositions of the Invention

The invention relates to a composition comprising spores of one or more *Bacillus* strains according to invention.

More specifically the invention relates to the following aspects with respect to compositions comprising *Bacillus* strains:

Aspect 5: A composition comprising spores of a *Bacillus* strain characterized in that:
  i) the *Bacillus* strain is non-hemolytic,
  ii) the *Bacillus* strain has antimicrobial activity against *Clostridium perfringens* and
  iii) the *Bacillus* strain improves body weight gain and/or feed conversion rate in chickens fed with the *Bacillus* strain.

Aspect 6: A composition comprising spores of a *Bacillus* strain characterized in that:
  i) the *Bacillus* strain is non-hemolytic,
  ii) the *Bacillus* strain has antimicrobial activity against *Clostridium perfringens* and
  iii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline.

Aspect 7: A composition comprising spores of a *Bacillus* strain characterized in that:
  i) the *Bacillus* strain is non-hemolytic,
  ii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline and
  iii) the *Bacillus* strain improves body weight gain and/or feed conversion rate in chickens fed with the *Bacillus* strain.

Aspect 8: A composition comprising spores of a *Bacillus* strain characterized in that:
  i) the *Bacillus* strain is non-hemolytic,
  ii) the *Bacillus* strain has antimicrobial activity against *Clostridium perfringens* and optionally
  iii) the *Bacillus* strain has enzymatic activity under aerobic and/or anaerobic conditions that hydrolyzes one or more of the substrates selected from the group consisting of Amylose, Arabinan, Arabinoxylan, Casein and Xylan.

In a preferred embodiment the *Bacillus* strain(s) of the composition according to Aspect 5, 6, 7 or 8 has a high compatibility with monensin such as being compatible with at least 2.3 µg/ml monensin as determined in Example 12. It is even more preferred that the *Bacillus* strain is compatible with at least 2.4 µg/ml monensin as determined in Example 12 (such as at least 2.5 µg/ml monensin as determined in Example 12, such as at least 2.6 µg/ml monensin as determined in Example 12 or such as at least 2.7 µg/ml monensin as determined in Example 12).

Sensitivity to Vancomycin, Clindamycin, Chloramphenicol, Gentamicin, Kanamycin, Streptomycin, Erythromycin and Tetracycline can, e.g., be determined as described in Example 5.

Enzymatic activity under aerobic and/or anaerobic conditions that hydrolyzes one or more of the substrates selected from the group consisting of Amylose, Arabinan, Arabinoxylan, Casein and Xylan can, e.g., be determined as described in Example 6.

In one embodiment the *Bacillus* strain of the composition according to Aspect 5, 6 or 7 has enzymatic activity under aerobic and/or anaerobic conditions that hydrolyzes one or more of the substrates selected from the group consisting of Amylose, Arabinan, Arabinoxylan, Casein and Xylan.

In one embodiment the *Bacillus* strain of the composition according to Aspect 6, 7, or 8 improves one or more performance parameters in poultry selected from the list consisting of body weight gain, European Production Efficacy Factor and feed conversion rate in chickens fed with the *Bacillus* strain.

In one embodiment the *Bacillus* strain of the composition according to Aspect 8 has antimicrobial activity against *Clostridium perfringens*. Antimicrobial activity against *Clostridium perfringens* can, e.g., be determined as described in Example 2.

In one embodiment the *Bacillus* strain of the composition according to Aspect 5 or 8 is sensitive to at least seven such as eight of the antibiotics selected from the group consisting of Vancomycin, Clindamycin, Chloramphenicol, Gentamicin, Kanamycin, Streptomycin, Erythromycin and Tetracycline.

In one embodiment the improvement of feed conversion rate (FCR) for Aspect 5, 6, 7 or 8 results in a FCR of −2.5% or less than −2.5%, such as less than −2.6%, such as less than −2.7%, such as less than −2.8%, such less than −2.9%, such as less than −3.0%. In a preferred embodiment the improvement of FCR results in a FCR of from −5% to −2% such as a FCR from −4% to −2%, such as a FCR of from −3.5% to −2.5%. In a specific embodiment the improvement of FCR for Aspect 1, 2, 3 or 4 results in a FCR within an interval selected from the group consisting of from −5% to −4.5%, from −4.5% to −4%, from −4% to −3.8%, from −3.8% to −3.6%, from −3.6% to −3.4%, from −3.4% to −3.2%, from −3.2 to −3.0%, from −3.0% to −2.8% and from −2.8 to −2.5%, or any combination of these intervals. The FCR can be determined as described in Example 8.

In one embodiment the improvement in body weight gain for Aspect 5, 6, 7 or 8 results in a body weight gain of at least 0.5%, such as at least 0.8%, such as at least 1.5%, such as at least 1.8%, such as at least 2.0%, such as at least 2.3%, such as at least 3.5%, such as at least 4.2%, such as at least 5.2%, such as at least 6.5%, such as at least 7.3%. In a preferred embodiment the improvement in body weight gain for Aspect 1, 2, 3 or 4 results in a body weight gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof. The body weight gain can be determined as described in Example 8.

In one embodiment the *Bacillus* strain of the composition according to Aspect 5, 6, 7 or 8 comprises 16S rDNA that has more than 98% (such as more than 98.5%, such as more than 99%, such as more than 99.5%) sequence identity to SEQ ID NO: 1 and/or more than 98% (such as more than 98.5%, such as more than 99%, such as more than 99.5%) sequence identity to SEQ ID NO: 2 and/or more than 98% (such as more than 98.5%, such as more than 99%, such as more than 99.5%) sequence identity to SEQ ID NO: 3 and/or more than 98% (such as more than 98.5%, such as more than 99%, such as more than 99.5%) sequence identity to SEQ ID NO: 4.

In one embodiment the *Bacillus* strain of the composition according to Aspect 5, 6, 7 or 8 is a *Bacillus subtilis* strain, or a *Bacillus amyloliquefaciens* strain.

In one embodiment the *Bacillus* strain of the composition according to Aspect 5, 6, 7 or 8 has antimicrobial effect against *E. coli*. The effect against *E. coli* can, e.g., be determined as described in Example 4.

In one embodiment the *Bacillus* strain of the composition according to Aspect 5, 6, 7 or 8 is the *Bacillus* strain having deposit accession number DSM 29869, or a strain having all of the identifying characteristics of *Bacillus* DSM 29869 or a mutant thereof that has antimicrobial activity against *Clostridium perfringens*. In another embodiment the *Bacillus* strain of the composition according to Aspect 5, 6, 7 or 8 is the *Bacillus* strain having deposit accession number DSM 29870, or a strain having all of the identifying characteristics of *Bacillus* DSM 29870 or a mutant thereof that has antimicrobial activity against *Clostridium perfringens*. In yet another embodiment the *Bacillus* strain of the composition according to Aspect 5, 6, 7 or 8 is the *Bacillus* strain having deposit accession number DSM 29871, or a strain having all of the identifying characteristics of *Bacillus* DSM 29871 or a mutant thereof that has antimicrobial activity against *Clostridium perfringens*. In a further embodiment the *Bacillus* strain of the composition according to Aspect 5, 6, 7 or 8 is the *Bacillus* strain having deposit accession number DSM 29872, or a strain having all of the identifying characteristics of *Bacillus* DSM 29872 or a mutant thereof that has antimicrobial activity against *Clostridium perfringens*.

The invention relates in one embodiment to a composition comprising a *Bacillus* having deposit accession number DSM 29869 or a strain having all of the identifying characteristics of *Bacillus* DSM 29869 or a mutant thereof. The invention relates in another embodiment to a composition comprising a *Bacillus* having deposit accession number DSM 29870 or a strain having all of the identifying characteristics of *Bacillus* DSM 29870 or a mutant thereof. The invention relates in another embodiment to a composition comprising a *Bacillus* having deposit accession number DSM 29871 or a strain having all of the identifying characteristics of *Bacillus* DSM 29871 or a mutant thereof. The invention relates in a further embodiment to a composition comprising a *Bacillus* having deposit accession number DSM 29872 or a strain having all of the identifying characteristics of *Bacillus* DSM 29872 or a mutant thereof.

In one embodiment of Aspect 5, 6, 7, or 8 the *bacillus* spores of the composition are present as dried spores such as spray-dried spores. In one embodiment of Aspect 5, 6, 7, or 8 the *bacillus* spores of the composition are present as stable spores. The composition according to Aspect 5, 6, 7, or 8 can also be a liquid composition and/or comprise culture supernatant comprising one or more *Bacillus* strain(s) of the invention.

In one embodiment of Aspect 5, 6, 7, or 8 the composition further comprises a carrier. The carrier can comprise one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, cellulose farigel, cassava cores, sodium aluminium silicate, colloidal amorphous silica, Sipernat 50S, polyethylene glycol 200, polyethylene glycol 400, polyethylene glycol 600, polyethylene glycol 1000, polyethylene glycol 1500, polyethylene glycol 4000 and carbopol.

In a preferred embodiment of Aspect 5, 6, 7, or 8 the composition further comprises calcium carbonate and sodium aluminium silicate.

In a preferred embodiment of Aspect 5, 6, 7, or 8 the composition further comprises calcium carbonate, sodium aluminium silicate and sucrose.

In another preferred embodiment of Aspect 5, 6, 7, or 8 the composition further comprises one or more carriers such as one or more carriers selected from the group consisting of Calcium carbonate, sodium sulfate, starch, farigel and cassava cores.

In another preferred embodiment of Aspect 5, 6, 7, or 8 the composition further comprises one or more flowability agents such as sodium aluminium silicate and/or colloidal amorphous silica (e.g., Sipernat 50S).

In another preferred embodiment of Aspect 5, 6, 7, or 8 the composition further comprises one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition comprises *Bacillus* DSM 29869, calcium carbonate and sodium aluminium silicate.

In a preferred embodiment the composition comprises *Bacillus* DSM 29869, calcium carbonate, sodium aluminium silicate and sucrose.

In a preferred embodiment the composition comprises *Bacillus* DSM 29869 and one or more carriers such as one or more carriers selected from the group consisting of calcium carbonate, sodium sulphate, starch, farigel and cassava cores.

In a preferred embodiment the composition comprises *Bacillus* DSM 29869 and one or more flowability agents such as sodium aluminium silicate and/or colloidal amorphous silica (e.g., Sipernat 50S).

In a preferred embodiment the composition comprises *Bacillus* DSM 29869 and one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition comprises *Bacillus* DSM 29870, calcium carbonate and sodium aluminium silicate.

In a preferred embodiment the composition comprises *Bacillus* DSM 29870, calcium carbonate, sodium aluminium silicate and sucrose.

In a preferred embodiment the composition comprises *Bacillus* DSM 29870 and one or more carriers such as one or more carriers selected from the group consisting of calcium carbonate, sodium sulphate, starch, farigel and cassava cores.

In a preferred embodiment the composition comprises *Bacillus* DSM 29870 and one or more flowability agents such as sodium aluminium silicate and/or colloidal amorphous silica (e.g., Sipernat 50S).

In a preferred embodiment the composition comprises *Bacillus* DSM 29870 and one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition comprises *Bacillus* DSM 29871, calcium carbonate and sodium aluminium silicate.

In a preferred embodiment the composition comprises *Bacillus* DSM 29871, calcium carbonate, sodium aluminium silicate and sucrose.

In a preferred embodiment the composition comprises *Bacillus* DSM 29871 and one or more carriers such as one or more carriers selected from the group consisting of calcium carbonate, sodium sulphate, starch, farigel and cassava cores.

In a preferred embodiment the composition comprises *Bacillus* DSM 29871 and one or more flowability agents such as sodium aluminium silicate and/or colloidal amorphous silica (e.g., Sipernat 50S).

In a preferred embodiment the composition comprises *Bacillus* DSM 29871 and one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition comprises *Bacillus* DSM 29872, calcium carbonate and sodium aluminium silicate.

In a preferred embodiment the composition comprises *Bacillus* DSM 29872, calcium carbonate, sodium aluminium silicate and sucrose.

In a preferred embodiment the composition comprises *Bacillus* DSM 29872 and one or more carriers such as one or more carriers selected from the group consisting of calcium carbonate, sodium sulphate, starch, farigel and cassava cores.

In a preferred embodiment the composition comprises *Bacillus* DSM 29872 and one or more flowability agents such as sodium aluminium silicate and/or colloidal amorphous silica (e.g., Sipernat 50S).

In a preferred embodiment the composition comprises *Bacillus* DSM 29872 and one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In one embodiment the composition comprises one or more coccidiostats wherein the composition is, e.g., a premix.

In a preferred embodiment the composition according to Aspect 5, 6, 7, or 8 the composition comprises from $10^5$ to $10^{18}$ CFU/g of isolated *Bacillus* spores.

In a further embodiment, the composition according to the invention comprises one or more bacterial strains such as at least two of the above strains up to and including all of the strains in the group consisting of DSM 29869, DSM 29870, DSM 29871 and DSM 29872.

In an embodiment to any of the aforementioned embodiments the *Bacillus* spore kills/inhibits at least 40% (such as at least 45%, at least 50%, at least 60%, at least 70% or at least 80%) of *Clostridium perfringens* after, e.g., 24 hours, e.g., determined as described in Example 2.

In another embodiment of the invention the composition further comprises one or more additional microbes. In another embodiment of the invention the composition further comprises one or more enzymes. In another embodiment of the invention the composition further comprises one or more vitamins. In another embodiment of the invention the composition further comprises one or more minerals. In another embodiment of the invention the composition further comprises one or more amino acids. In another embodiment of the invention the composition further comprises one or more other feed ingredients.

In an embodiment to any of the aforementioned embodiments, the composition also improves the health of the mono-gastric animal when fed to said animal. In another embodiment to any of the aforementioned embodiments, the composition also increases the egg yield of poultry when fed said poultry. In an embodiment to any of the aforementioned embodiments, the composition increases the meat yield of the mono-gastric animal when fed to said animal.

In a preferred embodiment, the composition comprises one or more bacterial strains described herein, wherein the bacterial count of each of the bacterial strains is between $1\times10^4$ and $1)(10^{18}$ CFU/kg of composition, preferably between $1\times10^7$ and $1)(10^{16}$ CFU/kg of composition, more preferably between $1\times10^{10}$ and $1\times10^{15}$ CFU/kg of composition and most preferably between $1\times10^{11}$ and $1\times10^{14}$ CFU/kg of composition.

In a preferred embodiment, the bacterial count of each of the bacterial strains in the composition is between $1\times10^4$ and $1\times10^{18}$ CFU/kg of dry matter, preferably between $1\times10^7$ and $1\times10^{16}$ CFU/kg of dry matter, more preferably between $1\times10^{10}$ and $1\times10^{15}$ CFU/kg of dry matter and most preferably between $1\times10^{11}$ and $1\times10^{14}$ CFU/kg of dry matter. In a more preferred embodiment the bacterial count of each of the bacterial strains in the animal feed is between $1 \times 10^8$ and $1 \times 10^{10}$ CFU/kg of dry matter.

In a preferred embodiment, the composition has a bacterial count of each *Bacillus* spore between $1 \times 10^3$ and $1 \times 10^{13}$ CFU/animal/day, preferably between $1 \times 10^5$ and $1 \times 10^{11}$ CFU/animal/day, more preferably between $1 \times 10^6$ and $1 \times 10^{10}$ CFU/animal/day and most preferably between $1 \times 10^7$ and $1 \times 10^9$ CFU/animal/day.

In still yet another embodiment of the invention, the one or more bacterial strains are present in the composition in form of a spore such as a stable spore. In still a further embodiment of the invention, the stable spore will germinate in the intestine and/or stomach of the mono-gastric animal.

In one embodiment, the one or more bacterial strains are stable when subjected to pressures applied/achieved during an extrusion process for pelleting. In a particular embodiment, the one or more bacterial strains are stable at pressures ranging from 1 bar to 40 bar, particularly 10 bar to 40 bar, more particularly 15 bar to 40 bar, even more particularly 20 bar to 40 bar, still even more particularly 35 bar to 37 bar, even still more particularly 36 bar.

In a particular embodiment, the one or more bacterial strains are stable at high temperatures. In particular, the bacterial strains are stable when they are subjected to temperatures achieved during an extrusion process for pelleting. In an even more particular embodiment, the one or more bacterial strains are stable at temperatures ranging from 80° C. to 120° C., particularly temperatures ranging from, 90° C. to 120° C., even more particularly temperatures ranging from 95° C. to 120° C.

In another aspect, the invention relates to a composition comprising a carrier and one or more of the bacteria cultures having characteristics substantially identical to that of a strain selected from the group consisting of:
the strain having the deposit accession number DSM 29869;
the strain having the deposit accession number DSM 29870;
the strain having the deposit accession number DSM 29871; and
the strain having the deposit accession number DSM 29872; or
any combination thereof.

In an embodiment, the composition comprises a carrier and the strain having the deposit accession number DSM 29869, or a strain having all of the identifying characteristics of *Bacillus* DSM 29869 or a mutant thereof.

In an embodiment, the composition comprises a carrier and the strain having the deposit accession number DSM 29870, or a strain having all of the identifying characteristics of *Bacillus* DSM 29870 or a mutant thereof.

In an embodiment, the composition comprises a carrier and the strain having the deposit accession number DSM 29871, or a strain having all of the identifying characteristics of *Bacillus* DSM 29871 or a mutant thereof.

In an embodiment, the composition comprises a carrier and the strain having the deposit accession number DSM 29872, or a strain having all of the identifying characteristics of *Bacillus* DSM 29872 or a mutant thereof.

In an embodiment, the composition further comprises one or more additional microbes. In a particular embodiment, the composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a particular embodiment, the composition further comprises a bacterium from one or more of the following strains of *Bacillus amyloliquefaciens, Bacillus subtilis, Bacillus pumilus, Bacillus polymyxa, Bacillus licheniformis, Bacillus megaterium, Bacillus coagulans, Bacillus circulans*, or any combination thereof.

In a particular embodiment, the composition further comprises one or more types of yeast. The one or more types of yeast can be selected from the group consisting of Saccharomycetaceae, *Saccharomyces* (such as *S. cerevisiae* and/or *S. boulardii*), *Kluyveromyces* (such as *K. marxianus* and *K. lactis*), *Candida* (such as *C. utilis*, also called *Torula* yeast), *Pichia* (such as *P. pastoris*), *Torulaspora* (such as *T. delbrueckii*), *Phaffia* yeasts and Basidiomycota.

In an embodiment to any of the aforementioned embodiments the composition further comprises a carrier. The carrier can comprise one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, cellulose, farigel, cassava cores, sodium aluminium silicate, colloidal amorphous silica, Sipernat 50S, polyethylene glycol 200, polyethylene glycol 400, polyethylene glycol 600, polyethylene glycol 1000, polyethylene glycol 1500, polyethylene glycol 4000 and carbopol.

In another embodiment, the composition described herein can optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch, The ENZYME database, 2000, *Nucleic Acids Res.* 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy (ModO) internet site (Coutinho, P. M. & Henrissat, B. (1999) Carbohydrate-Active Enzymes server at URL: http://afmb.cnrs-mrs.fr/~cazy/CAZY/index.html (corresponding papers: Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation", K. Ohmiya, K. Hayashi, K. Sakka, Y. Kobayashi, S. Karita and T. Kimura eds., Uni Publishers Co., Tokyo, pp. 15-23).

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P and HiPhos™ (DSM Nutritional Products), Natuphos™ (BASF), Finase® and Quantum® Blue (AB Enzymes), the Phyzyme® XP (Verenium/DuPont) and Axtra® PHY (DuPont). Other preferred phytases include those described in, e.g., WO 98/28408, WO 00/43503, and WO 03/066847.

In a particular embodiment, the composition of the invention comprises a xylanase (EC 3.2.1.8). Examples of commercially available xylanases include Ronozyme® WX and G2 (DSM Nutritional Products), Econase® XT and Barley (AB Vista), Xylathin® (Verenium) and Axtra® XB (Xylanase/beta-glucanase, DuPont)

In a particular embodiment, the composition of the invention comprises a protease (EC 3.4). Examples of commercially available proteases include Ronozyme® ProAct (DSM Nutritional Products).

Manufacturing

The composition of the invention can, e.g., be manufactured as mash composition (non-pelleted) or pelleted composition. The bacteria cultures and optionally enzymes can be added as solid or liquid formulations. For example, for mash composition a solid or liquid culture formulation may be added before or during the ingredient mixing step. Typically a liquid culture preparation comprises the culture of the invention optionally with a polyol, such as glycerol, ethylene glycol or propylene glycol, and is added after the pelleting step, such as by spraying the liquid formulation onto the pellets.

The enzyme may be added to the composition as a granule, which is optionally pelleted or extruded. The granule typically comprises a core particle and one or more coatings, which typically are salt and/or wax coatings. The core particle can either be a homogeneous blend of an active compound optionally together with salts (e.g., organic or inorganic zinc or calcium salt) or an inert particle with an active compound applied onto it. The active compound is the culture of the invention optionally combined with one or more enzymes. The inert particle may be water soluble or water insoluble, e.g., starch, a sugar (such as sucrose or lactose), or a salt (such as NaCl, $Na_2SO_4$). The salt coating is typically at least 1 μm thick and can either be one particular salt or a mixture of salts, such as $Na_2SO_4$, $K_2SO_4$, $MgSO_4$ and/or sodium citrate. Other examples are those described in, e.g., WO 2008/017659, WO 2006/034710, WO 97/05245, WO 98/54980, WO 98/55599, WO 00/70034 or polymer coating such as described in WO 01/00042.

PREFERRED EMBODIMENTS

Preferred embodiments of the invention are described in the two set of items herein below.

Item Set I:

1. A *Bacillus* strain characterized in that:
   i) the *Bacillus* strain is non-hemolytic,
   ii) the *Bacillus* strain has antimicrobial activity against *Clostridium perfringens* and
   iii) the *Bacillus* strain improves body weight gain and/or feed conversion rate in chickens fed with the *Bacillus* strain.

2. A *Bacillus* strain characterized in that:
   i) the *Bacillus* strain is non-hemolytic,
   ii) the *Bacillus* strain has antimicrobial activity against *Clostridium perfringens* and
   iii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline.

3. A *Bacillus* strain characterized in that:
   i) the *Bacillus* strain is non-hemolytic,
   ii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline and
   iii) the *Bacillus* strain improves body weight gain and/or feed conversion rate in chickens fed with the *Bacillus* strain.

4. A *Bacillus* strain characterized in that:
   i) the *Bacillus* strain is non-hemolytic,
   ii) the *Bacillus* strain has antimicrobial activity against *Clostridium perfringens* and optionally
   iii) the *Bacillus* strain has enzymatic activity under aerobic and/or anaerobic conditions that hydrolyzes one or more of the substrates selected from the group consisting of Amylose, Arabinan, Arabinoxylan, Casein and Xylan.

5. The *Bacillus* strain according to any of items 1 to 3, wherein the *Bacillus* strain has enzymatic activity under aerobic and/or anaerobic conditions that hydrolyzes one or more of the substrates selected from the group consisting of Amylose, Arabinan, Arabinoxylan, Casein and Xylan (e.g., determined as described in Example 6).

6. The *Bacillus* strain according to any of items 2 to 4, wherein the *Bacillus* strain improves one or more performance parameters in poultry selected from the list consisting of body weight gain, European Production Efficacy Factor and feed conversion rate in poultry fed with the *Bacillus* strain.

7. The *Bacillus* strain according to item 3, wherein the *Bacillus* strain has antimicrobial activity against *Clostridium perfringens* (e.g., determined as described in Example 2).

8. The *Bacillus* strain according to any of items 1 and 4, wherein the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline (e.g., determined as described in Example 5).

9. The *Bacillus* strain according to any of the previous items, wherein the *Bacillus* strain comprises 16S rDNA that is more than 98% sequence identity to SEQ ID NO: 1 and/or more than 98% sequence identity to SEQ ID NO: 2 and/or more than 98% sequence identity to SEQ ID NO: 3 and/or more than 98% sequence identity to SEQ ID NO: 4.

10. The *Bacillus* strain according to any of the previous items, wherein the *Bacillus* strain is a *Bacillus subtilis* strain or a *Bacillus amyloliquefaciens* strain.

11. The *Bacillus* strain according to any of the previous items, wherein the *Bacillus* strain has antimicrobial effect against *E. coli* (e.g., determined as described in Example 4).

12. The *Bacillus* strain according to any of the previous items, wherein the *Bacillus* strain is the *Bacillus* strain having deposit accession number DSM 29869, or a strain having all of the identifying characteristics of *Bacillus* DSM 29869 or a mutant thereof that has antimicrobial activity against *Clostridium perfringens*.

13. The *Bacillus* strain according to any of the previous items, wherein the *Bacillus* strain is the *Bacillus* strain having deposit accession number DSM 29870, or a strain having all of the identifying characteristics of *Bacillus* DSM 29870 or a mutant thereof that has antimicrobial activity against *Clostridium perfringens*.

14. The *Bacillus* strain according to any of the previous items, wherein the *Bacillus* strain is the *Bacillus* strain having deposit accession number DSM 29871, or a strain having all of the identifying characteristics of *Bacillus* DSM 29871 or a mutant thereof that has antimicrobial activity against *Clostridium perfringens*.

15. The *Bacillus* strain according to any of the previous items, wherein the *Bacillus* strain is the *Bacillus* strain having deposit accession number DSM 29872, or a strain having all of the identifying characteristics of *Bacillus* DSM 29872 or a mutant thereof that has antimicrobial activity against *Clostridium perfringens*.

16. A *Bacillus* having deposit accession number DSM 29869 or a strain having all of the identifying characteristics of *Bacillus* DSM 29869 or a mutant thereof.

17. A *Bacillus* having deposit accession number DSM 29870 or a strain having all of the identifying characteristics of *Bacillus* DSM 29870 or a mutant thereof.

18. A *Bacillus* having deposit accession number DSM 29871 or a strain having all of the identifying characteristics of *Bacillus* DSM 29871 or a mutant thereof.

19. A *Bacillus* having deposit accession number DSM 29872 or a strain having all of the identifying characteristics of *Bacillus* DSM 29872 or a mutant thereof.

20. The *Bacillus* strain according to any of the previous items, wherein the *Bacillus* strain has a high compatibility with monensin such as being compatible with at least 2.3 µg/ml monensin as determined in Example 12 (such as at least 2.4 µg/ml monensin, such as at least 2.5 µg/ml monensin, such as at least 2.6 µg/ml monensin or such as at least 2.7 µg/ml monensin as determined in Example 12).

21. A composition comprising spores of the *Bacillus* strain according to any of items 1-20.

22. The composition according to item 21, wherein the *Bacillus* spores of the composition are present as dried spores.

23. The composition according to any of items 21 to 22 which further comprises a carrier.

24. The composition according to item 23, wherein the carrier comprises one or more of the following compounds: water, glycerol, ethylene glycol, 1,2-propylene glycol or 1,3-propylene glycol, sodium aluminium silicate, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, farigel, cassava cores, sodium aluminium silicate, colloidal amorphous silica, Sipernat 50S, polyethylene glycol 200, polyethylene glycol 400, polyethylene glycol 600, polyethylene glycol 1000, polyethylene glycol 1500, polyethylene glycol 4000, carbopol and cellulose.

25. The composition according to any of items 21 to 24, wherein the composition comprises from $10^5$ to $10^{18}$ CFU/g of isolated *Bacillus* spores.

26. The composition according to any of items 21 to 25 which further comprises one or more components selected from the list consisting of:
   one or more enzymes;
   one or more additional microbes;
   one or more vitamins;
   one or more minerals;
   one or more amino acids; and
   one or more other feed ingredients.

27. The composition according to any of items 21 to 26, wherein the bacterial count of each *Bacillus* spore is between $1 \times 10^4$ and $1 \times 10^{18}$ CFU/kg of composition, preferably between $1 \times 10^7$ and $1 \times 10^{16}$ CFU/kg of composition, more preferably between $1 \times 10^{10}$ and $1 \times 10^{15}$ CFU/kg of composition and most preferably between $1 \times 10^{11}$ and $1 \times 10^{14}$ CFU/kg of composition.

28. The composition according to any of items 21 to 26, wherein the bacterial count of each *Bacillus* spore is between $1 \times 10^4$ and $1 \times 10^{18}$ CFU/kg of composition, preferably between $1 \times 10^6$ and $1 \times 10^{15}$ CFU/kg of composition, and more preferably between $1 \times 10^7$ and $1 \times 10^{11}$ CFU/kg of composition.

29. A biologically pure culture of the *Bacillus* strain according to any of items 1 to 20.

30. An isolated *Bacillus* strain according to any of items 1 to 20.

31. An isolated *Bacillus* strain selected from the group consisting of *Bacillus* strain DSM 29869, DSM 29870, DSM 29871 and DSM 29872, or a strain having all of the identifying characteristics of *Bacillus* DSM 29869, DSM 29870, DSM 29871 and DSM 29872 or a mutant thereof.

32. The isolated *Bacillus* strain according to item 31, wherein the identifying characteristics can one or more (such as all) of the characteristics selected from the group consisting of
   i) non-hemolytic, e.g., as determined in Example 1,
   ii) antimicrobial activity against *Clostridium perfringens*, e.g., as determined in Example 2,
   iii) antimicrobial activity against *E. coli*, e.g., as determined in Example 4,
   iv) sensitive to Vancomycin, Clindamycin, Chloramphenicol, Gentamicin, Kanamycin, Streptomycin, Erythromycin and Tetracyclin, and
   v) high compatibility with monensin such as being compatible with at least 2.3 µg/ml monensin as determined in Example 12 (such as at least 2.4 µg/ml monensin, such as at least 2.5 µg/ml monensin, such as at least 2.6 µg/ml monensin or such as at least 2.7 µg/ml monensin as determined in Example 12).

Item Set II:

1. A *Bacillus* strain characterized in:
   i) having deposit accession number DSM 29870 or a strain having all of the identifying characteristics of *Bacillus* DSM 29870 or a mutant thereof;
   ii) having deposit accession number DSM 29869 or a strain having all of the identifying characteristics of *Bacillus* DSM 29869 or a mutant thereof;
   iii) having deposit accession number DSM 29871 or a strain having all of the identifying characteristics of *Bacillus* DSM 29871 or a mutant thereof; or
   iv) having deposit accession number DSM 29872 or a strain having all of the identifying characteristics of *Bacillus* DSM 29872 or a mutant thereof.

2. The *Bacillus* strain according to item 1, wherein the *Bacillus* strain is non-hemolytic.

3. The *Bacillus* strain according to any of the previous items, wherein the *Bacillus* strain has antimicrobial activity against *Clostridium perfringens* (e.g., determined as described in Example 2).

4. The *Bacillus* strain according to any of the previous items, wherein the *Bacillus* strain improves body weight gain and/or feed conversion rate in chickens fed with the *Bacillus* strain.

5. The *Bacillus* strain according to any of the previous items, wherein the *Bacillus* strain comprises 16S rDNA that is more than 98% sequence identity to SEQ ID NO: 1 and/or more than 98% sequence identity to SEQ ID NO: 2 and/or more than 98% sequence identity to SEQ ID NO: 3 and/or more than 98% sequence identity to SEQ ID NO: 4.

6. The *Bacillus* strain according to any of the previous items, wherein the *Bacillus* strain comprises 16S rDNA that is more than 99% sequence identity to SEQ ID NO: 1 and/or more than 99% sequence identity to SEQ ID NO: 2 and/or more than 99% sequence identity to SEQ ID NO: 3 and/or more than 99% sequence identity to SEQ ID NO: 4.

7. The *Bacillus* strain according to any of the previous items, wherein the *Bacillus* strain is a *Bacillus subtilis* strain or a *Bacillus amyloliquefaciens* strain.

8. The *Bacillus* strain according to any of the previous items, wherein the *Bacillus* strain has antimicrobial effect against *E. coli* (e.g., determined as described in Example 4).

9. The *Bacillus* strain according to any of the previous items, wherein the *Bacillus* strain is an isolated *Bacillus* strain.

10. A biologically pure culture of the *Bacillus* strain according to any of items 1 to 9.

11. The *Bacillus* strain according to any of the previous items, wherein the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline (e.g., determined as described in Example 5).

12. The *Bacillus* strain according to any of the previous items, wherein the *Bacillus* strain has enzymatic activity under aerobic and/or anaerobic conditions that hydrolyzes one or more of the substrates selected from the group consisting of Amylose, Arabinan, Arabinoxylan, Casein and Xylan (e.g., determined as described in Example 6).

13. The *Bacillus* strain according to any of the previous items, wherein the *Bacillus* strain improves one or more performance parameters in poultry selected from the list consisting of body weight gain, European Production Efficacy Factor and feed conversion rate in poultry fed with the *Bacillus* strain.

14. The *Bacillus* strain according to any of the previous items, wherein the *Bacillus* strain has a high compatibility with monensin such as being compatible with at least 2.3 µg/ml monensin as determined in Example 12 (such as at least 2.4 µg/ml monensin, such as at least 2.5 µg/ml monensin, such as at least 2.6 µg/ml monensin or such as at least 2.7 µg/ml monensin as determined in Example 12).

15. A composition comprising spores of the *Bacillus* strain according to any of items 1-14.

16. The composition according to item 15, wherein the *Bacillus* spores of the composition are present as spores such as dried spores such as spray dried spores.

17. The composition according to item 16, wherein the bacterial count of each *Bacillus* spore is between $1\times10^4$ and $1\times10^{18}$ CFU/kg of composition, preferably between $1\times10^6$ and $1\times10^{15}$ CFU/kg of composition, and more preferably between $1\times10^7$ and $1\times10^{11}$ CFU/kg of composition.

18. The composition according to any of items 15 to 17 which further comprises a carrier.

19. The composition according to item 18, wherein the carrier comprises one or more of the following compounds: water, glycerol, ethylene glycol, 1,2-propylene glycol or 1,3-propylene glycol, sodium aluminium silicate, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, farigel, cassava cores, sodium aluminium silicate, colloidal amorphous silica, Sipernat 50S, polyethylene glycol 200, polyethylene glycol 400, polyethylene glycol 600, polyethylene glycol 1000, polyethylene glycol 1500, polyethylene glycol 4000, carbopol. and cellulose.

20. The composition according to item 18 or 19, wherein the carrier comprises calcium carbonate.

21. The composition according to any of items 15 to 20, wherein the composition comprises from $10^5$ to $10^{18}$ CFU/g of isolated *Bacillus* spores.

22. The composition according to any of items 15 to 21 which further comprises one or more components selected from the list consisting of:
   one or more enzymes;
   one or more additional microbes;
   one or more vitamins;
   one or more minerals;
   one or more amino acids; and
   one or more other feed ingredients.

23. The composition according to any of items 15 to 22, wherein the bacterial count of each *Bacillus* spore is between $1\times10^4$ and $1\times10^{18}$ CFU/kg of composition, preferably between $1\times10^7$ and $1\times10^{16}$ CFU/kg of composition, more preferably between $1\times10^{10}$ and $1\times10^{15}$ CFU/kg of composition and most preferably between $1\times10^{11}$ and $1\times10^{14}$ CFU/kg of composition.

24. The composition according to any of items 15 to 23, wherein the bacterial count of each *Bacillus* spore is between $1\times10^4$ and $1\times10^{18}$ CFU/kg of composition, preferably between $1\times10^6$ and $1\times10^{15}$ CFU/kg of composition, and more preferably between $1\times10^7$ and $1\times10^{11}$ CFU/kg of composition.

25. An isolated *Bacillus* strain selected from the group consisting of *Bacillus* strain DSM 29869, DSM 29870, DSM 29871 and DSM 29872, or a strain having all of the identifying characteristics of *Bacillus* DSM 29869, DSM 29870, DSM 29871 and DSM 29872 or a mutant thereof.

26. The isolated *Bacillus* strain according to item 25, wherein the identifying characteristics can one or more (such as all) of the characteristics selected from the group consisting of
   i) non-hemolytic, e.g., as determined in Example 1,
   ii) antimicrobial activity against *Clostridium perfringens*, e.g., as determined in Example 2,
   iii) antimicrobial activity against *E. coli*, e.g., as determined in Example 4,
   iv) sensitive to Vancomycin, Clindamycin, Chloramphenicol, Gentamicin, Kanamycin, Streptomycin, Erythromycin and Tetracyclin, and
   v) high compatibility with monensin such as being compatible with at least 2.3 µg/ml monensin as determined in Example 12 (such as at least 2.4 µg/ml monensin, such as at least 2.5 µg/ml monensin, such as at least 2.6 µg/ml monensin or such as at least 2.7 µg/ml monensin as determined in Example 12).

27. The isolated *Bacillus* strain according to item 25 or 26 for use of treatment of necrotic enteritis and/or a *Clostridium perfringens* infection.
28. An isolated *Bacillus* strain selected from the group consisting of *Bacillus* strain DSM 29869, DSM 29871 and DSM 29872, or a strain having all of the identifying characteristics of *Bacillus* DSM 29869, DSM 29871 and DSM 29872 or a mutant thereof for treatment of necrotic enteritis and/or a *Clostridium perfringens* infection.
29. Use of the *Bacillus* strain or the composition according to any of the previous items to improve one or more performance parameters of an animal selected from the group consisting of: improving the feed conversion ratio, improving the body weight gain, improving the European Production Efficacy Factor, improving the feed efficiency and improving the health, e.g., of poultry such as chickens.
30. The use according to item 29, wherein the *Bacillus* strain is selected from the group consisting of *Bacillus* strain DSM 29869, DSM 29871 and DSM 29872, or a strain having all of the identifying characteristics of *Bacillus* DSM 29869, DSM 29871 and DSM 29872 or a mutant thereof.
31. A method of improving one or more performance parameters of an animal selected from the group consisting of: improving the feed conversion ratio, improving the body weight gain, improving the European Production Efficacy Factor, improving the feed efficiency and improving the health, comprising administering the *Bacillus* strain or the composition according to any of the previous items to the animal.
32. The method according to item 31, wherein the *Bacillus* strain is selected from the group consisting of *Bacillus* strain DSM 29869, DSM 29871 and DSM 29872, or a strain having all of the identifying characteristics of *Bacillus* DSM 29869, DSM 29871 and DSM 29872 or a mutant thereof.
33. A method for feeding an animal comprising administering the *Bacillus* strain or the composition according to any of the previous items to said animal optionally in conjunction with other animal feed ingredients.
34. The method for feeding an animal according to item 33 wherein the animal is selected from the group consisting of poultry and swine.

EXAMPLES

Example 1: Screening for Hemolysis Negative *Bacillus* Strains

Hemolysis was tested according to the Technical Guidance on the assessment of the toxigenic potential of *Bacillus* species used in animal nutrition, EFSA Journal 2011; 9(11): 2445.
Sheep blood agar plates were purchased as ready to use (Becton Dickenson art 254053 or 254087). Alternatively, the agar plates can be prepared by adding 5% defibrinated sheep blood (obtained from Statens Serum Institute, Denmark) to TS-agar (Oxoid CM 131). Agar should be autoclaved at 121° C. for 20 minutes and cooled down to about 40° C. before adding the blood immediately before pouring the plates.
The *Bacillus* strains were taken from the preservation at −80° C. and streaked on TS-agar plate, which was incubated at 30° C. overnight or until growth appeared. From a single colony as little as possible of the material was used to streak a line on ¼ of an agar plate. The plate was incubated at 30° C. for 72 hours. Hemolysis/clearing zones of the *Bacillus* strains to be tested were compared with the positive and negative control. As positive control *Bacillus subtilis* ATCC21332 was used. As negative control *Bacillus subtilis* 168, (BGSC-1A1, *Bacillus* Genetic Stock Center) was used.
In a screening of 599 independent isolates of *Bacillus* 223 strains (37%) were hemolysis negative. In another screening 21 of 65 independent isolates of *Bacillus* (32%) were hemolysis negative. Both screenings exclusively comprised strains that based on identification by 16S rDNA sequencing belong to *Bacillus subtilis, Bacillus licheniformis, Bacillus pumilus* or *Bacillus amyloliquefaciens* or close relatives to these four species.
The non-Hemolytic *Bacillus* strains therefore seem to be common and fairly abundant in nature, but only comprising a minority of the natural strains. The non-hemolytic strains seem to be more abundant in *Bacillus licheniformis*, while most *Bacillus amyloliquefaciens* strains appear hemolytic. All the non-hemolytic strains were tested for inhibition of growth of *Clostridium perfringens*. The following strains from screening were all hemolysis negative and among those selected for further studies: DSM 29869, DSM 29870, DSM 29871 and DSM 29872. Clostat (*Bacillus* PB6) was determined to be hemolytic.

Example 2: Determination of Inhibition of Growth of *Clostridium perfringens*

All the non-hemolytic strains were tested for inhibition of growth of *Clostridium perfringens* strains 23 and 48 (both are netB positive) [Gholamiandekhordi et al., 2006, Molecular and phenotypical characterization of *Clostridium perfringens* isolates from poultry flocks with different diseasestatus, *Vet. Microbiol.* 113:143-152], were grown overnight in tryptic soy broth (BD part 211822) supplemented with 0.6% yeast extract (BD part 212750) at 35° C. under static anaerobic conditions. 250 µL of the overnight culture of *Clostridium perfringens* was added to 250 mL of tryptic soy agar supplemented with 0.6% yeast extract at 40° C. and poured into rectangular petri plates (Nunc part 267060). The inoculated agar was allowed to cool at room temperature after which an 8 mm diameter well was made in the agar. Plates were stored in absence of oxygen until use.
The *Bacillus* strain DSM 29869, DSM 29870, DSM 29871, or DSM 29872 was grown overnight in tryptic soy broth at 35° C. under aerobic conditions. 1000 µL of *Bacillus* culture was collected and fractionated into cell-free supernatant and cells by centrifugation. 20 µL of cell-free supernatant or 100× diluted cells in phosphate buffered saline were added directly to the wells in the *Clostridium perfringens* inoculated agar plates. A control well contained 20 µL of phosphate buffer saline. The plates were incubated for 18 hours at 35° C. under anaerobic conditions.
Inhibition of the *Clostridium perfringens* strain was noted by a circular clearing zone around the well of interest. The phosphate buffer saline well was considered a negative control based on lack of clearing zone around the well.
Cell-free supernatant and 100× diluted cells of *Bacillus* strains DSM 29869, DSM 29870, DSM 29871, and DSM 29872 were able to consistently inhibit growth of *C. perfringens* strains 23 and 48 in vitro. Inhibition was also seen by competitor strain "CloSTAT", for both supernatant and cells, but was not seen with competitor strain GalliproTect. "CloSTAT" is a strain of *Bacillus amyloliquefaciens* that was isolated from the commercial DFM product CloSTAT, Kemin. "GalliproTect" is a strain of *Bacillus licheniformis* that was isolated from the commercial product Gallipro Tect, Chr Hansen.

Example 3: Identification, Characterization and Deposit of the Biological Material

*Bacillus amyloliquefaciens* strain O52BCT was deposited on Jan. 12, 2015, under the terms of the Budapest Treaty on the International Recognition of the Deposit of Microorganisms for the Purposes of Patent Procedure at the Leibniz-Institut, Deutsche Sammlung von Mikroorganismen und Zellkurturen GmbH, Inhoffenstraβe 7 B, 38124 Braunschweig, Germany. The strain was designated deposit accession number DSM 29869 on Jan. 14, 2015. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

*Bacillus subtilis* strain O52BCU was deposited on Jan. 12, 2015, under the terms of the Budapest Treaty on the International Recognition of the Deposit of Microorganisms for the Purposes of Patent Procedure at the Leibniz-Institut, Deutsche Sammlung von Mikroorganismen und Zellkurturen GmbH, Inhoffenstraβe 7 B, 38124 Braunschweig, Germany. The strain was designated deposit accession number DSM 29870 on Jan. 14, 2015. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

*Bacillus subtilis* strain O52BCV was deposited on Jan. 12, 2015, under the terms of the Budapest Treaty on the International Recognition of the Deposit of Microorganisms for the Purposes of Patent Procedure at the Leibniz-Institut, Deutsche Sammlung von Mikroorganismen und Zellkurturen GmbH, Inhoffenstraβe 7 B, 38124 Braunschweig, Germany. The strain was designated deposit accession number DSM 29871 on Jan. 14, 2015. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

*Bacillus amyloliquefaciens* strain O52ESV was deposited on Jan. 12, 2015, under the terms of the Budapest Treaty on the International Recognition of the Deposit of Microorganisms for the Purposes of Patent Procedure at the Leibniz-Institut, Deutsche Sammlung von Mikroorganismen und Zellkurturen GmbH, Inhoffenstraβe 7 B, 38124 Braunschweig, Germany. The strain was designated deposit accession number DSM 29872 on Jan. 14, 2015. The strain was deposited under conditions that assure access to the cultures will be available during the pendency of this patent application to one determined by the Commissioner of Patents and Trademarks to be entitled thereto under 37 C.F.R. § 1.14 and 35 U.S.C. § 122. Each deposit represents a pure or substantially pure culture of the deposited strain. Each deposit is available as required by foreign patent laws in countries wherein counterparts of the subject application or its progeny are filed. However, it is to be understood that the availability of a deposit does not constitute a license to practice the subject invention in derogation of patent rights granted by governmental action.

Sequencing of 16S rDNA Genes

DNA was extracted from a culture of DSM 29869, DSM 29870, DSM 29871 and DSM 29872 using QiaAmp DNA Blood Mini Kit (Qiagen art 51106). The kit was used as recommended for extraction of DNA from gram positive bacteria.

16S rDNA was amplified in a total volume of 50 µl by mixing: 10 pmol of each of Primer 16S F and 16S R, 0.2 mM of each nucleotide, 2.5 units Ampli taq, 1× Ampli taq buffer, 5 µl DNA template and by using the following PCR program: 94° C. 2 min (94° C. 30 s, 52° C. 30 S, 72° C. 1 min)×35, 72° C. 10 min on a Perkin Elmer PCR machine. The PCR product was sequenced by Novozymes DNA sequencing facility using primer 530R, 357F, 1390R and 1100F.

TABLE 3.2

Primers:

| Primer | Sequence | SEQ ID NO |
| --- | --- | --- |
| 16S-F | 5'-GAGTTTGATCCTGGCTCAG-3' | SEQ ID NO: 8 |
| 16S-R | 5'-AGAAAGGAGGTGATCCAGCC-3' | SEQ ID NO: 9 |
| 794-R | 5'-ATCTAATCCTGTTTGCTCCCC-3' | SEQ ID NO: 10 |
| 357-F | 5'-TACGGGAGGCAGCAG-3' | SEQ ID NO: 11 |
| 1390-R | 5'-CGGTGTGTRCAAGGCCC-3' | SEQ ID NO: 12 |
| 1000-F | 5'-CAACGAGCGCAACCCT', | SEQ ID NO: 13 |

Degeneration of primer 1390-R: R is A or G. The 16 S rDNA sequences from DSM 29869, DSM 29870, DSM 29871 and DSM 29872 are shown as SEQ ID NO: 1-4 in the sequence listing respectively. The 16 S rDNA sequences from DSM 29869, DSM 29870, DSM 29871 and DSM 29872 were analyzed by BLAST against EMBL database and showed identity to 16 S rDNA sequences of *Bacillus subtilis* (SEQ ID NO: 2 and SEQ ID NO: 3) and to *Bacillus amyloliquefaciens* (SEQ ID NO: 1 and SEQ ID NO: 4).

In order to study the phylogenetic affiliation of SEQ ID NO: 1 to SEQ ID NO: 4 the sequences were analyzed by a ClustalW alignment in MegAlign (DNASTAR) using SEQ ID NO: 5 to SEQ ID NO: 7 as benchmark. These sequences are reference 16S rDNA sequences of the type strains of *Bacillus vallismortis* taken from AB021198 (SEQ ID NO: 5), *Bacillus subtilis* taken from AJ276351 (SEQ ID NO: 6) and *Bacillus amyloliquefaciens* taken from AB255669 (SEQ ID NO: 7).

The ClustalW alignment of SEQ ID NO: 1 to SEQ ID NO: 7 (FIG. 1) shows 7 nucleotide positions where 2 or more sequences have a nucleotide that deviates from the other. For numbering the positions in SEQ ID NO: 6 are used. At position 152 SEQ ID NO: 2 is identical to *Bacillus amyloliquefaciens* and *Bacillus vallismortis*, but different from the rest that are identical to each other. At position 174 SEQ ID NO: 1 and SEQ ID NO: 4 are identical to *Bacillus amyloliquefaciens*, but different from the rest that are identical to each other. At position 257 SEQ ID NO: 4 is identical to *Bacillus amyloliquefaciens*, but different from the rest that are identical to each other. At position 437, 444 and 455 SEQ ID NO: 2 and SEQ ID NO: 3 are identical to *Bacillus subtilis*, but different from the rest that are identical to each other. At position 1223 SEQ ID NO: 1 is identical to *Bacillus amyloliquefaciens*, but different from the rest that are identical to each other. The variation in the 16S rDNA genes support the species affiliation seen in the BLAST report.

Description of the Biological Material

*Bacillus amyloliquefaciens* DSM 29869 was isolated by Novozymes (Novo Nordisk) from an environmental sample collected at Jamaica in 1990. The strain was identified as *Bacillus amyloliquefaciens* based on 16S rDNA sequencing.

*Bacillus subtilis* DSM 29870 was isolated by Novozymes (Novo Nordisk) from an environmental sample collected at Jamaica in 1990. The strain was identified as *Bacillus subtilis* based on 16S rDNA sequencing.

*Bacillus subtilis* DSM 29871 was isolated for Novozymes by a Danish high-school student at Brønderslev Gymnasium from a soil sample from private property in Denmark in 2008. The strain was identified as *Bacillus subtilis* based on 16S rDNA sequencing.

*Bacillus amyloliquefaciens* DSM 29872 was isolated from an environmental sample from the USA in 2008. The strain was identified as *Bacillus amyloliquefaciens* based on 16S rDNA sequencing.

Example 4: Determination of Inhibition of Growth of *Escherichia coli*

*Escherichia coli* strains, ATCC10536 or ATCC25922, were grown overnight in tryptic soy broth (BD part 211822) supplemented with 0.6% yeast extract (BD part 212750) at 35° C. under static anaerobic conditions. 100 µL of the overnight culture of *Escherichia coli* was added to 250 mL of tryptic soy agar supplemented with 0.6% yeast extract at 40° C. and poured into rectangular petri plates (Nunc part 267060). The inoculated agar was then allowed to cool at room temperature after which an 8 mm diameter well was made in the agar.

The *Bacillus* strain DSM 29869, DSM 29870, DSM 29871, or DSM 29872 was grown overnight in tryptic soy broth at 35° C. under aerobic conditions. 1000 µL of *Bacillus subtilis* culture was collected and fractionated into cell-free supernatant and cells by centrifugation. 20 µL of cell-free supernatant or 100× diluted cells in phosphate buffer saline were added directly to the wells in the *Escherichia coli* inoculated agar plates. A control well contained 20 µL of phosphate buffer saline. The plates were incubated for 18 hours at 30° C. under aerobic conditions.

Inhibition of the *Escherichia coli* strain was noted by a circular clearing zone around the well of interest. The phosphate buffer saline well was considered a negative control based on lack of clearing zone around the well.

Cell-free supernatant and 100× diluted cells of *Bacillus* strains DSM 29869, DSM 29870, DSM 29871, and DSM 29872 were able to consistently inhibit growth of the *E. coli* strains ATCC10535 and ATCC25922 in vitro. Inhibition was also seen by competitor strain CloSTAT, for both supernatant and cells.

Example 5: Sensitivity to Antibiotics

The minimal inhibitory concentrations (MIC) of eight antibiotics against *Bacillus* strains DSM 29869, DSM 29870, DSM 29871, and DSM 29872 were determined using broth micro dilution essentially as described in the CLSI guidelines (M07-A9 Methods for Dilution Antimicrobial Susceptibility Tests for Bacteria That Grow Aerobically; 2012). Only modification was that volumes were changed; 90 µl Mueller Hinton Broth 2 with bacteria was added to 10 µl antibiotics dilutions, cfu's of bacteria and concentration of antibiotics were changed so final concentrations and final cfu's matched the guideline. The plates were incubated for 20-24 h instead of 16-20 h. The control strain recommended in the CLSI standard *Staphylococcus aureus* ATCC 29213 was used as control strain.

Strains:
  *Bacillus amyloliquefaciens* DSM 29869
  *Bacillus subtilis* DSM 29870
  *Bacillus subtilis* DSM 29871
  *Bacillus amyloliquefaciens* DSM 29872
  *S. aureus* ATCC 29213

Antibiotics:
  Chloramphenicol (Sigma C1919, 10 mg/ml, solubilized in 96% ethanol)
  Clindamycin (Sigma PHR1159, 10 mg/ml, solubilized in water)
  Erythromycin (ABBOTICIN from Amdipharm 40501, 50 mg/ml, solubilized in 96% ethanol)
  Gentamycin (Biomedicals inc., 190057, 10 mg/ml, solubilized in water)
  Kanamycin (Sigma, CAS no. 25389-94-0, 50 mg/ml, solubilized in water)
  Streptomycin (Sigma, S1277, 10 mg/ml, solubilized in water)
  Tetracycline (Sigma, T3383, 10 mg/ml, solubilized in water)
  Vancomycin (Sigma, V-8138, 10 mg/ml, solubilized in water)
  Mueller Hinton Broth 2 (Sigma/Fluka 90922)
  0.9% NaCl (Sigma/RdH 31434/Merck 106404)
  Tryptone soya agar plates (Oxoid CM 131)
  Microtiter plates: Costar plate, polypropylene, round bottom, Corning 3879

Preparation of Bacteria:

A few colonies of *Bacillus* spp. (<1 day old) were inoculated into Mueller Hinton Broth 2 (MHB) and incubated for around 4 hours at 37° C. $OD_{600}$ (BioPhotometer plus, Eppendorf) was measured and adjusted to 0.25 (equivalent to McFarland 0.5) in MHB. For the control strain direct colony suspension was used. A few colonies of *S. aureus* ATCC 29213 (<1 day old) were suspended in MHB and $OD_{600}$ (BioPhotometer plus, Eppendorf) was measured and adjusted to 0.10-0.12 (equivalent to McFarland 0.5) in MHB. The bacterial suspensions were diluted 200× in MHB.

Preparation of Assay Plates:

Antibiotics were diluted to the concentration of 640 µg/mL in MHB. A two fold dilution series was prepared in MHB down to the concentration 0.625 µg/ml. 10 µl of each dilution and of each antibiotic was pipetted into a micro-titre plate. Later, when the antibiotics were mixed with the suspension of bacteria, the samples were diluted 10× (10 μL sample in a total volume of 100 μl). This resulted in the final test range of 0.06-64 μg/ml.

If the plates were not used right away the plates were stored in the freezer at −20° C. until usage.

90 μl of the bacterial suspensions were added to the assay plates. The assay plates were incubated in a plastic bag with at wet cloth at 37° C. for 20-24 h. The MIC was determined as the lowest concentration of antibiotic that completely inhibited growth of bacteria as detected by the unaided eye.

Cfu Estimation:

A 10-fold dilution series in 0.9% NaCl was made to the $10^{-3}$ of the cultures inoculated into the micro-titre plate. 2×100 ul from the $10^{-3}$ dilution were plated onto two TSA plates. The plates were incubated overnight at 37° C. Number of CFU/ml was counted.

Three biological replicates of the assay were performed for *Bacillus subtilis* DSM 29871, *Bacillus amyloliquefaciens* DSM 29869 and *Bacillus subtilis* DSM 29870 (MIC 1-3), while four biological replicates were performed for *Bacillus amyloliquefaciens* DSM 29872 (MIC 2-5).

Results:

The MIC values obtained for *B. subtilis* DSM 29870 showed that the breakpoint values were equal to or below the breakpoint values given in the EFSA guideline (EFSA journal 2012; 10(6):2740). For *B. subtilis* DSM 29869 the MIC values obtained in two out of the three biological replicates showed MIC values equal to or below the breakpoint. In MIC 1 the value for Tetracycline was 16. However, due to analytical variance of the method MIC results of one dilution above the breakpoint is in general accepted and the strain may be regarded as being sensitive. Thus, according to EFSA these two strains are regarded as sensitive to all the 8 antibiotics included in the test (Tables 5.2 and 5.3).

For the strains *B. subtilis* DSM 29871 and *B. amyloliquefaciens* DSM 29872 the MIC values showed that the two strains were sensitive to seven out of the eight antibiotics (Tables 5.1 and 5.4). An increased tolerance was observed towards Streptomycin and according to EFSA the strains are classified as resistant to Streptomycin.

As a control *S. aureus* ATCC 29213 was tested in parallel and had MIC values within the ranges given by the CLSI standard (M100-S24 Performance Standards for Antimicrobial Susceptibility Testing; informational Supplement, 2014) (Table 5.5).

The amount of bacteria inoculated into the assay plates was measured (CFU/ml). In general the CFU/ml was very close to the target value of $5*10^5$ CFU/ml. However, the CFU/ml for *Bacillus* strains may be associated with some uncertainty, since the bacteria tend to aggregate and once aggregated will only result in one colony forming unit (Tables 5.1 and 5.2).

TABLE 5.1

MIC results for *B. subtilis* DSM 29871

| Antibiotic | MIC 1 μg/ml | MIC 2 μg/ml | MIC 3 μg/ml | EFSA* breakpoints μg/ml |
|---|---|---|---|---|
| Chloramphenicol | 8 | 4 | 8 | 8 |
| Clindamycin | 0.5 | 0.25 | 0.5 | 4 |
| Erythromycin | 0.125 | 0.125 | 0.125 | 4 |
| Gentamycin | 0.25 | 0.125 | 0.25 | 4 |
| Kanamycin | 2 | 1 | 2 | 8 |
| Streptomycin | 32 | 16 | 32 | 8 |
| Tetracycline | 2 | 4 | 4 | 8 |
| Vancomycin | 0.25 | 0.25 | 0.25 | 4 |
| CFU/ml | $3.6 * 10^5$ | n.r. | n.r. | |

*EFSA Journal 2012; 10(6):2740 n.r. not registered

TABLE 5.2

MIC results for *B. amyloliquefaciens* DSM 29869

| Antibiotic | MIC 1 μg/ml | MIC 2 μg/ml | MIC 3 μg/ml | EFSA* breakpoints μg/ml |
|---|---|---|---|---|
| Chloramphenicol | 4 | 4 | 4 | 8 |
| Clindamycin | 1 | 0.5 | 1 | 4 |
| Erythromycin | 0.5 | 0.06 | 0.06 | 4 |
| Gentamycin | 0.5 | 0.125 | 0.06 | 4 |
| Kanamycin | 2 | 0.5 | 0.5 | 8 |
| Streptomycin | 2 | 4 | 4 | 8 |
| Tetracycline | 16 | 8 | 8 | 8 |
| Vancomycin | 0.25 | 0.25 | 0.25 | 4 |
| CFU/ml | $3.9 * 10^5$ | $2.7 * 10^5$ | $1.2 * 10^5$ | |

*EFSA Journal 2012; 10(6):2740

TABLE 5.3

MIC results for *B. subtilis* DSM 29870

| Antibiotic | MIC 1 μg/ml | MIC 2 μg/ml | MIC 3 μg/ml | EFSA* breakpoints μg/ml |
|---|---|---|---|---|
| Chloramphenicol | 4 | 8 | 4 | 8 |
| Clindamycin | 0.25 | 0.25 | 0.25 | 4 |
| Erythromycin | 0.125 | 0.125 | 0.125 | 4 |
| Gentamycin | 0.25 | 0.125 | 0.25 | 4 |
| Kanamycin | 2 | 1 | 2 | 8 |
| Streptomycin | 4 | 4 | 8 | 8 |
| Tetracycline | 0.25 | 0.25 | 0.25 | 8 |
| Vancomycin | 0.25 | 0.25 | 0.25 | 4 |
| CFU/ml | $4.2 * 10^5$ | $2.1 * 10^5$ | $1.4 * 10^5$ | |

*EFSA Journal 2012; 10(6):2740

TABLE 5.4

MIC results for *B. amyloliquefaciens* DSM 29872

| Antibiotic | MIC 2 µg/ml | MIC 3 µg/ml | MIC 4 µg/ml | MIC 5 µg/ml | EFSA* breakpoints µg/ml |
|---|---|---|---|---|---|
| Chloramphenicol | 4 | 4 | 4 | 4 | 8 |
| Clindamycin | 0.5 | 0.5 | 0.5 | 0.5 | 4 |
| Erythromycin | 0.06 | 0.125 | 0.06 | 0.06 | 4 |
| Gentamycin | 0.06 | 0.06 | 0.125 | 0.125 | 4 |
| Kanamycin | 1 | 0.5 | 2 | 1 | 8 |
| Streptomycin | 8 (32) | 8 | 32 | >64 | 8 |
| Tetracycline | 0.25 | 0.25 | 0.125 | 0.125 | 8 |
| Vancomycin | 0.25 | 0.25 | 0.125 | 0.125 | 4 |
| CFU/ml | $2.7 * 10^5$ | $1.5 * 10^5$ | $4.7 * 10^5$ | $6.3 * 10^5$ | |

*EFSA Journal 2012; 10(6):2740

TABLE 5.5

MIC results for *S. aureus* ATCC 29213

| Antibiotic | MIC 1 µg/ml | MIC 2 µg/ml | MIC 3 µg/ml | MIC 4 µg/ml | MIC 5 µg/ml | CLSI* breakpoints µg/ml |
|---|---|---|---|---|---|---|
| Chloramphenicol | 8-16 | 16 | 8 | 16 | 16 | 2-16 |
| Clindamycin | 0.125 | 0.25 | 0.125 | 0.06 | 0.06 | 0.06-0.25 |
| Erythromycin | 0.5 | 0.5 | 0.5 | 0.5 | 0.5 | 0.25-1 |
| Gentamycin | 0.5 | 0.5 | 0.5 | 1 | 1 | 0.12-1 |
| Kanamycin | 4 | 4 | 4 | 4 | 4 | 1-4 |
| Streptomycin | 8 | 8 | 8 | 16 | 8 | No information |
| Tetracycline | 0.5 | 1 | 1 | 0.5 | 0.5 | 0.12-1 |
| Vancomycin | 0.5 | 1 | 1 | 1 | 1 | 0.5-2 |
| CFU/ml | $5.2*10^5$ | $7.0*10^5$ | $7.0*10^5$ | $7.3*10^5$ | $4.3*10^5$ | |

*M100-S24 Performance Standards for Antimicrobial Susceptibility Testing; informational Supplement, 2014

Example 6: Enzyme Activity

Preparation of Overnight Pre-Cultures

Overnight cultivation was made in a 96-deep well plate with 1.25 mL of LB broth (Difco; BD #244610) per well. Each strain was tested in duplicate and inoculated with a single colony from a pure Standard Methods Agar plate (SMA plates, Smith River Biologicals #11-00450). Before incubation, a single sterile Aeraseal breathable seal (Fisher #50-212-463) was placed on top of the plate, and the plate was incubated with shaking at 35° C. overnight under aerobic conditions.

Determination of Anaerobic Growth

SMA plates were streaked from the overnight cultures using a 10 µL inoculating loop. Up to four strains were streaked per plate, into separate quadrants.

Plates were incubated at 39° C. in an AnaeroJar (Thermo Scientific Oxoid, Fisher #OXAG0025A) along with an AnaeroGen sachet (Thermo Scientific Oxoid, Fisher #OXAN0025A) to maintain anaerobic conditions (~0.1% oxygen). Work was performed under aseptic conditions in biological hood, using sterile materials.

Enzyme Activity Determination Using AZCL-Substrate Agar Plates

Preparation of media with AZCL substrates which can be autoclaved AZCL-cellulose (AZCL-HE-Cellulose, I-AZ-CEL, Megazyme), arabinoxylan (AZCL-Arabinoxylan, wheat, I-AZWAX, Megazyme), arabinan (AZCL-Arabinan, debranched, I-AZDAR, Megazyme):

Into two (2) 500 mL beakers, 300 mL of 0.1× and 1× LB agar were prepared for each beaker, with a magnetic stir bars added to each. While stirring, 100 mL of LB condition from the beakers were added to three (3) 250 mL Wheaton bottles, thus giving 3 bottles with 0.1× LB and 3 bottles with 1× LB. AZCL-cellulose, arabinan, and arabinoxylan were then added separately to each of a 1× and a 0.1× bottle with stirring. A total of 0.05 grams of substrate is added per 100 mL of media. If more than 100 mL of media is being used, the amount of substrate added is adjusted by using the 0.05 g/100 mL ratio. The media were autoclaved to sterilize. Note: Only these three AZCL substrates can be autoclaved without obvious dye release indicating substrate instability. After autoclaving, media is kept at ≥50° C. until ready to pour plates. The pH was checked, and if necessary adjusted to pH 7 using 10% HCl or 2N NaOH, maintaining sterility.

Preparation of Media with AZCL Substrates which Can't be Autoclaved

These substrates were: AZCL-amylose (I-AZAMY, Megazyme), AZCL-casein (I-AZCAS, Megazyme), AZCL-xylan (Xylan, birchwood (I-AZXBW, Megazyme)

Into two (2) 1000 mL Wheaton bottles, 400 mL of 0.1× LB and 1× LB was prepared and a magnetic stir bar was added to each. The media was autoclaved to sterilize, prior to adding AZCL reagent. After autoclaving, media was kept at 50-55° C. until ready to add AZCL substrate and pour plates. The pH was checked, and if necessary adjusted to pH 7 using 10% HCl or 2N NaOH, maintaining sterility.

Pouring AZCL Substrate Media Agar Plates

Work was performed under aseptic conditions in biological hood, using sterile materials. These steps were done relatively quickly, so that the agar did not solidify before transferring into the 96-well plate.

For substrates which could be autoclaved (AZCL-cellulose, AZCL-arabinoxylan, AZCL-arabinan): The warm (~50° C.), autoclaved liquid agar media was magnetically stirred in order to suspend the insoluble AZCL substrate. An aliquot was transferred to a sterile solution basin (Periodic mixing of the material in the solution basin was necessary to keep the substrate suspended.) A repeating, multi-channel pipette (e.g., Matrix 1250 μL pipet along with the corresponding 1250 μL sterile pipet tips) was used to dispense 180 μL into each well of a sterile 96-well plate. A set of tips would typically last for up to six columns per plate. Once the plate was filled, a sterile lid was added, and it was allowed to solidify. One plate was made for each substrate (AZCL-cellulose, AZCL-arabinoxylan, AZCL-arabinan) and condition (0.1× and 1× LB).

For the substrates that could not be autoclaved (AZCL-amylose, AZCL-casein, AZCL-xylan): Into a sterile 250 mL beaker with magnetic stir-bar was added 100 mL of warm, sterile 0.1× or 1× LB media (no AZCL substrate added). With stirring, add 0.05 mg of AZCL substrate, and continue stirring until re-suspended. It may help to add the substrate slowly at first. Once substrate was re-suspended, it was poured into solution basin and added to plates as described above. One plate was made for each substrate (AZCL-cellulose, AZCL-arabinoxylan, AZCL-arabinan) and condition (0.1× and 1× LB).

Inoculating the 96-Well Plates, Incubation, and Evaluation

Work was performed under aseptic conditions in biological hood, using sterile materials. The AZCL substrate agar plates were inoculated by applying 2 μL of overnight culture that was dispensed on top of the agar. The added liquid should be visible on top of the agar. When moving to the next plate, be sure that there are no drops left at the end of the pipet tips to ensure that each well has been inoculated. Repeat for all AZCL substrate plates. Control enzyme dilutions were prepared, each at 1/100, diluting in sterile phosphate dilution buffer: 10 μL enzyme preparation+990 μL buffer. Control enzyme wells were then inoculated with 10 μL of the appropriate enzyme dilution for each substrate

TABLE 6.1

Enzymes and respective substrates

| Enzyme | Substrate |
| --- | --- |
| Amylase | Amylose |
| Arabinase | Arabinan |
| Cellulase | Cellulose |
| Protease | Casein |
| Xylanase | Arabinoxylan, Xylan |

TABLE 6.2

Enzyme production under aerobic conditions

30° C. Aerobic, 24 h

| organism ID | Amylose | Arabinan | Arabinoxylan | Casein | Cellulose | Xylan |
| --- | --- | --- | --- | --- | --- | --- |
| DSM 29869 | + | + | + | + | − | + |
| DSM 29870 | + | + | + | + | − | + |
| DSM 29871 | + | + | + | + | + | + |
| DSM 29872 | + | + | + | + | − | + |

TABLE 6.3

Enzyme production under anaerobic conditions, 24 hours

30° C. Anaerobic, 24 h

| organism ID | Amylose | Arabinan | Arabinoxylan | Casein | Cellulose | Xylan |
| --- | --- | --- | --- | --- | --- | --- |
| DSM 29869 | + | + | + | − | − | + |
| DSM 29870 | + | + | +/− | + | − | + |
| DSM 29871 | − | + | + | − | + | + |
| DSM 29872 | + | + | + | − | − | + |

TABLE 6.4

Enzyme production under anaerobic conditions, 48 hours

30° C. Anaerobic, 48 h

| organism ID | Amylose | Arabinan | Arabinoxylan | Casein | Cellulose | Xylan |
| --- | --- | --- | --- | --- | --- | --- |
| DSM 29869 | + | + | + | + | − | + |
| DSM 29870 | + | + | +/− | + | − | + |
| DSM 29871 | − | + | + | − | + | + |
| DSM 29872 | + | + | + | − | − | + |

Example 7: Efficacy of the DSM 29870 Strain in *Clostridium perfringens* Challenge Conditions Material and Methods Three independent battery studies have been conducted to evaluate the influence of the strain DSM 29870 on the development of an induced necrotic enteritis.

In each experiment, a total of 256 one day-old male broiler chickens Cobb×Cobb were allocated to Petersime battery cages (8 birds/cage). Cages were used in factorial and completely randomized design with 8 cages per treatment (i.e., 64 animals/treatment).

An unmedicated corn/soybean meal-based commercial broiler starter ration was formulated (Table 7.1). Feed and water were available ad libitum throughout the trials.

TABLE 7.1

Composition of the basal experimental diet[4] (starter d1-d28)

|  | Starter (0-28) |
|---|---|
| Ingredients |  |
| Corn, yellow, ground | 56.12 |
| Soybean meal (48) | 37.50 |
| Fat, poultry | 3.00 |
| Dicalcium phosphate | 1.75 |
| Limestone | 0.80 |
| Salt | 0.30 |
| Vitamin premix[1] | 0.25 |
| DL-Methionine | 0.20 |
| Trace mineral premix[2] | 0.08 |
| Calculated Nutritional Content |  |
| ME, kcal/kg | 3.096 |
| Protein, % | 22.30 |
| Lysine, % | 1.180 |
| Methionine, % | 0.530 |
| Met + Cys, %[3] | 0.890 |

[1]Vitamin mix provided the following (per kg of diet): thiamin·mononitrate, 2.4 mg; nicotinic acid, 44 mg; riboflavin, 4.4 mg; D-Ca pantothenate, 12 mg; vitamin $B_{12}$ (cobalamin), 12.0 µg; pyridoxine·HCL, 4.7 mg; D-biotin, 0.11 mg; folic acid, 5.5 mg; menadione sodium bisulfite complex, 3.34 mg; choline chloride, 220 mg; cholecalciferol, 27.5 ug; trans-retinyl acetate, 1,892 ug; all-rac α tocophetyl acetate, 11 mg; ethoxyquin, 125 mg.
[2]Trace mineral mix provided the following (per kg of diet): manganese ($MnSO_4·H_2O$), 60 mg; iron ($FeSO_4·7H_2O$), 30 mg; zinc (ZnO), 50 mg; copper ($CuSO_4·5H_2O$), 5 mg; iodine (ethylene diamine dihydroiodide), 0.15 mg; selenium ($NaSe0_3$), 0.3 mg.
[3]Met = methionine; Cys = cysteine.
[4]The basal feed will not contain any probiotic/prebiotic feed additives, NSPases, coccidiostats or antibiotic growth promoter.

The 4 experimental groups consisted in (Table 7.2): T1, non-infected and non-treated animals; T2, *C. perfringens* infected and non-treated animals; T3, *C. perfringens* infected animals fed with the basal diet containing bacitracin (included at 50 ppm, from d1 to d28); T4, *C. perfringens* infected animals fed with the basal diet containing the DSM 29870 strain (included at $1·10^9$ CFU/kg of feed in trial 1 and $5·10^8$ CFU/kg of feed in trials 2 and 3, from d1 to d28).

TABLE 7.2

Experimental treatments

| Treatments |  |
|---|---|
| T1 | Non-infected, non-treated |
| T2 | Infected, non-treated |
| T3 | Infected, bacitracin |
| T4 | Infected, DSM 29870 |

On day 14, all birds were orally inoculated with a coccidial inoculum containing approximately 5,000 oocysts of *Eimeria maxima* per bird.

Once daily on d19, d20 and d21, all birds, except T1, were administered (by oral gavage) 1 mL of a fresh broth culture of *C. perfringens*.

On d21, three birds from each cage were selected, sacrificed, weighed, and examined for the degree of presence of necrotic enteritis lesions. The scoring was based on a 0 to 3 score, with 0 being normal and 3 being the most severe.

The live body weight and the feed were recorded at the start (d1) and the end of the experiment (d28), on a cage basis, to calculate performance:

Body Weight Gain (BWG)=(Live Body Weight)$_{d28}$−(Live Body Weight)$_{d1}$

Feed Conversion Ratio (FCR)=ratio between feed consumed and weight gained Mortality was recorded daily and the FCR was adjusted accordingly.

Necrotic enteritis lesion scores, total mortality and % of dead birds with necrotic enteritis lesions were also calculated Data (n=32) were subjected to an ANOVA, with complete randomized block design using the ANOVA procedure of XLSTAT (Addinsoft 1995-2014) to establish differences between diets. Pen was considered as the experimental unit. The model included diets (n=4) and block as fixed effect. Results are reported as least square means. LS means were assumed to be different at P 0.05.

Experimental Results

The results obtained on performance, necrotic enteritis lesion scores, mortality and % of dead birds with necrotic enteritis lesions parameters are shown in Tables 7.3.

TABLES 7.3

Effect of dietary supplementation of the strain DSM 29870 on the negative impact on production parameters due to induced necrotic enteritis in three independent trials.

| Trial 1 | BWG[5] (g/bird) (d1-d28) | FCR[5] (d1-d28) | Lesion score[6] (d21) | Total mortality (%) (d1-d28) | Dead birds with necrotic enteritis lesions (%) (d1-d28) |
|---|---|---|---|---|---|
| T1[1] | 720a | 1.666c | 0.0a | 7.5b | 0.0b |
| T2[2] | 549b | 2.071a | 0.2a | 27.5a | 17.2a |
| T3[3] | 633ab | 1.813bc | 0.2a | 5.0b | 1.6b |
| T4[4] | 628ab | 1.843bc | 0.3a | 5.0b | 3.1b |

[1]Non-infected, non-treated group fed with the basal diet.
[2]Infected, non-treated group fed with the basal diet.
[3]Infected group fed with the basal diet supplemented with bacitracin (50 ppm).
[4]Infected group fed with the basal diet supplemented with DSM 29870 ($1.10^9$ CFU/kg of feed).
[5]Means from 8 replicates of 8 birds per cage for each group. Raw data (n = 32) were analyzed using variance analysis with block (n = 8) and treatments (n = 4) as fixed effect.
[6]Means from 8 replicates of 3 birds per cage for each group. Raw data (n = 32) were analyzed using variance analysis with block (n = 8) and treatments (n = 4) as fixed effect.
a, b, cValues with different superscripts are significantly (P < 0.05) different from each other.

| Trial 2 | BWG[5] (g/bird) (d1-d28) | FCR[5] (d1-d28) | Lesion score[6] (d21) | Total mortality (%) (d1-d28) | Dead birds with necrotic enteritis lesions (%) (d1-d28) |
|---|---|---|---|---|---|
| T1 | 685a | 1.692b | 0.0d | 2.5c | 0.0c |
| T2 | 435c | 2.404a | 1.2a | 32.5a | 20.3a |

-continued

| Trial 2 | BWG[5] (g/bird) (d1-d28) | FCR[5] (d1-d28) | Lesion score[6] (d21) | Total mortality (%) (d1-d28) | Dead birds with necrotic enteritis lesions (%) (d1-d28) |
|---|---|---|---|---|---|
| T3 | 665ab | 1.759b | 0.6b | 12.5bc | 6.3c |
| T4 | 654ab | 1.768b | 0.4bc | 25.0ab | 9.4bc |

[1]Non-infected, non-treated group fed with the basal diet.
[2]Infected, non-treated group fed with the basal diet.
[3]Infected group fed with the basal diet supplemented with bacitracin (50 ppm).
[4]Infected group fed with the basal diet supplemented with DSM 29870 (5.10[8] CFU/kg of feed).
[5]Means from 8 replicates of 8 birds per cage for each group. Raw data (n = 32) were analyzed using variance analysis with block (n = 8) and treatments (n = 4) as fixed effect.
[6]Means from 8 replicates of 3 birds per cage for each group. Raw data (n = 32) were analyzed using variance analysis with block (n = 8) and treatments (n = 4) as fixed effect.
a, b, cValues with different superscripts are significantly ($P < 0.05$) different from each other.

| Trial 3 | BWG[5] (g/bird) (d1-d28) | FCR[5] (d1-d28) | Lesion score[6] (d21) | Total mortality (%) (d1-d28) | Dead birds with necrotic enteritis lesions (%) (d1-d28) |
|---|---|---|---|---|---|
| T1 | 667a | 1.752c | 0.0b | 10.0a | 0.0c |
| T2 | 521b | 1.988a | 0.5a | 25.0a | 15.6a |
| T3 | 645a | 1.786bc | 0.6a | 15.0a | 4.7bc |
| T4 | 638a | 1.851b | 0.4a | 10.0a | 4.7bc |

[1]Non-infected, non-treated group fed with the basal diet.
[2]Infected, non-treated group fed with the basal diet.
[3]Infected group fed with the basal diet supplemented with bacitracin (50 ppm).
[4]Infected group fed with the basal diet supplemented with DSM 29870 (5.10[8] CFU/kg of feed).
[5]Means from 8 replicates of 8 birds per cage for each group. Raw data (n = 32) were analyzed using variance analysis with block (n = 8) and treatments (n = 4) as fixed effect.
[6]Means from 8 replicates of 3 birds per cage for each group. Raw data (n = 32) were analyzed using variance analysis with block (n = 8) and treatments (n = 4) as fixed effect.
a, b, cValues with different superscripts are significantly ($P < 0.05$) different from each other.

The data obtained from the three challenge studies showed that the strain DSM 29870 can counteract the negative impact of an induced necrotic enteritis on the production parameters with a significant effect in all challenge trials on the FCR and the mortality due to necrotic enteritis, relative to the positive control group (non-infected, non-treated animals).

Furthermore, there was no significant difference between the DSM 29870 fed group and the bacitracin fed group with regards to all parameters measured in these trials.

The challenge studies described above showed that the administration of the DSM 29870 strain could prevent necrotic enteritis in broiler chickens.

Example 8: First Performance Trial with Broiler Chickens (521)

Material and Methods

A total of 2000 one day-old male broiler chickens Cobb 500 were individually weighed (body weight 42 g±1 g) and allocated in floor pens (50 birds/pen). Pens were used in factorial and completely randomized design with 8 pens per treatment (i.e., 400 animals/treatment). The 5 experimental treatments consisted in (Table 8.1): T1, negative control basal diets; T2, basal diets containing the strain DSM 29870 (included at 5·10[8] CFU/kg of feed, from d1 to d35); T3, basal diets containing the strain DSM 29871 (included at 5·10[8] CFU/kg of feed, from d1 to d35); T4 basal diets containing the strain DSM 29872 (included at 5·10[8] CFU/kg of feed, from d1 to d35); T5, basal diet containing a marketed probiotic, GalliPro Max (included at the commercial dose, 8·10[8] CFU/kg of feed, from d1 to d35).

Basal diets consisted in 3 phases feeding program: starter phase (from 1 to day 12), grower phase (from 13 to day 28) and finisher phase (from 29 to day 35). Every phases were formulated to meet or exceed animal requirement and agree with standard commercial US corn-soybean meal-based broiler diets. The dietary and raw material composition of these diets is given in Table 8.2. All experimental diets include phytase (Ronozyme P, 250 FYT/kg) and did not contain any coccidiostat, NSPase or growth promoting substance. Feed and water were available ad libitum throughout the trial.

TABLE 8.1

Experimental treatments
Treatments

| T1 | Control |
| T2 | T1 + DSM 29870 |
| T3 | T1 + DSM 29871 |
| T4 | T1 + DSM 29872 |
| T5 | T1 + GalliPro Max |

TABLE 8.2

Composition of the basal experimental diets

| Ingredients | Starter (0-12 d) % | Grower (13-28 d) % | Finisher (29-35 d) % |
|---|---|---|---|
| Corn, yellow, grain | 64.673 | 66.460 | 68.491 |
| Soybean meal, dehulled, solvent | 29.020 | 26.662 | 24.677 |
| Ampro 55 (animal by-product 55% protein) | 2.500 | 3.000 | 3.000 |
| Calcium carbonate | 0.886 | 0.735 | 0.684 |
| Fat, vegetable | 0.883 | 1.485 | 1.702 |
| Dicalcium phosphate | 0.706 | 0.612 | 0.500 |
| Salt, plain (NaCl) | 0.439 | 0.435 | 0.436 |
| Methionine MHA | 0.358 | 0.259 | 0.221 |
| L-Lysine | 0.273 | 0.208 | 0.145 |
| L-Threonine 98.5 | 0.103 | 0.000 | 0.000 |
| Trace Mineral[1] | 0.075 | 0.075 | 0.075 |
| Vitamin premix[2] | 0.065 | 0.050 | 0.050 |
| Ronozyme P-(ct) | 0.019 | 0.019 | 0.019 |
| Calculated Nutritional Content | | | |
| ME (kcal/kg) | 3,067 | 3,130 | 3,165 |
| Crude protein (%) | 20.96 | 20.03 | 19.16 |
| Dig. Lysine (%) | 1.20 | 1.10 | 1.00 |
| Dig. Methionine (%) | 0.61 | 0.52 | 0.48 |
| Dig. TSAA (%) | 0.90 | 0.80 | 0.75 |
| Dig. Threonine (%) | 0.81 | 0.68 | 0.65 |
| Calcium (%) | 0.90 | 0.85 | 0.8 |
| Avail. phosphorus (%) | 0.42 | 0.42 | 0.4 |

[1]Vitamin mix will provide the following (per kg of diet): thiamin•mononitrate, 2.4 mg; nicotinic acid, 44 mg; riboflavin, 4.4 mg; D-Ca pantothenate, 12 mg; vitamin $B_{12}$ (cobalamin), 12.0 µg; pyridoxine•HCL, 4.7 mg; D-biotin, 0.11 mg; folic acid, 5.5 mg; menadione sodium bisulfite complex, 3.34 mg; choline chloride, 220 mg; cholecalciferol, 27.5 ug; trans-retinyl acetate, 1,892 ug; all-rac α tocophetyl acetate, 11 mg; ethoxyquin, 125 mg.
[2]Trace mineral mix provided the following (per kg of diet): manganese ($MnSO_4 \cdot H_2O$), 60 mg; iron ($FeSO_4 \cdot 7H_2O$), 30 mg; zinc (ZnO), 50 mg; copper ($CuSO_4 \cdot 5H_2O$), 5 mg; iodine (ethylene diamine dihydroiodide), 0.15 mg; selenium ($NaSeO_3$), 0.3 mg.

The live body weight and the feed were recorded at the start (d1) and the end of the experiment (d35), on a pen basis, to calculate performance:

Feed Intake (FI)=(Remaining Feed)$_{d35}$−(Issued Feed)$_{d1}$
Body Weight Gain (BWG)=(Live Body Weight)$_{d35}$−(Live Body Weight)$_{d1}$
Feed Conversion Ratio (FCR)=ratio between feed consumed and weight gained Mortality was recorded daily and the FCR was adjusted accordingly.

Data (n=40) were subjected to an ANOVA, with complete randomized block design using the ANOVA procedure of XLSTAT (Addinsoft 1995-2014) to establish differences between diets. Pen was considered as the experimental unit. The model included diets (n=5) and block as fixed effect. Results are reported as least square means. LS means were assumed to be different at P 0.05.

Similar calculations were realized in the example 9 and 10.
Similar Calculations were Realized in the Example 3 and 4.
Experimental Results The results obtained on performance parameters for the whole experimental period are shown in Table 8.3.

TABLE 8.3

Effect of dietary supplementation of the strains DSM 29870, DSM 29871 and DSM 29872 on broiler performance

| Parameters[4] | Control[1] | DSM 29870[2] supplemented group | DSM 29871[2] supplemented group | DSM 29872[2] supplemented group | GalliPro Max[3] supplemented group |
|---|---|---|---|---|---|
| FI (g/bird) | 3245a | 3256a | 3221a | 3263a | 3203a |
| Relative to the control | — | +0.3% | −0.7% | +0.6% | −1.3% |
| BWG (g/bird) | 1987ab | 2026ab | 2002ab | 2038a | 1973b |
| Relative to the control | — | +2.0% | +0.8% | +2.6% | −0.7% |
| FCR | 1.633a | 1.607b | 1.609b | 1.602b | 1.624ab |
| Relative to the control | — | −1.6% | −1.5% | −2.0% | −0.6% |
| Mortality (%) | 3.25a | 3.50a | 5.25a | 4.5a | 6.25a |

[1]Group fed with the basal diet.
[2]DSM 29870/29871/29872 supplemented group fed with the basal diet including strain DSM 29870/29871/29872 at 5·10[8] CFU/kg of feed.
[3]GalliPro Max supplemented group fed with the basal diet including GalliPro Max at 8·10[8] CFU/kg of feed.
[4]Means from 8 replicates of 50 birds per pen for each group. Raw data (n = 24) were analyzed using variance analysis with block (n = 8) and treatments (n = 3) as fixed effect.
a, b, cValues with different superscripts are significantly (P < 0.05) different from each other.

Feed additives did not significantly affect animal feed intake relative to the control. Body weight was slightly increased using the NZB strains whereas GalliPro Max tended to decrease this parameter.

The DSM 29870, DSM 29871 and DSM 29872 strains also improved significantly the feed conversion ratio by 1.6%, 1.5% and 1.9%, respectively, with no significant differences between the groups fed with NZB strains. GalliPro Max had only a slight and non-significant effect on the feed conversion ratio.

None of the probiotic tested here had a significant effect on the mortality level.

Example 9: Second Performance Trial with Broiler Chickens (522)

Material and Methods

A total of 900 one day-old male broiler chickens Ross 708 were individually weighed (body weight 47.1±1.1 g) and allocated in floor pens (15 birds/pens). Pens were used in factorial and completely randomized design with 12 pens per treatment (i.e., 180 animals/treatment). The 5 experimental treatments consisted in (Table 9.1): T1, negative control basal diets; T2, basal diets containing the strain DSM 29870 (included at 5·10[8] CFU/kg of feed, from d1 to d35); T3, basal diets containing the strain DSM 29871 (included at 5·10[8] CFU/kg of feed, from d1 to d35); T4 basal diets containing the strain DSM 29872 (included at 5·10[8] CFU/kg of feed, from d1 to d35); T5, basal diet containing a marketed probiotic, GalliPro Max (included at the commercial dose, 8·10[8] CFU/kg of feed, from d1 to d35).

Basal diets consisted in 3 phases feeding program: starter phase (from 1 to day 14), grower phase (from 15 to day 21) and finisher phase (from 22 to day 35). Every phases were formulated to meet or exceed animal requirement and agree with standard commercial US corn-soybean meal-based broiler diets. The dietary and raw material composition of these diets is given in Table 9.2. All experimental diets included vitamin and mineral premixes, but did not contain any coccidiostat, NSPase, phytase or growth promoting substance. Feed and water were available ad libitum throughout the trial.

TABLE 9.1

Experimental treatments

| | Treatments |
|---|---|
| T1 | Control |
| T2 | T1 + DSM 29870 |
| T3 | T1 + DSM 29871 |
| T4 | T1 + DSM 29872 |
| T5 | T1 + GalliPro Max |

TABLE 9.2

Composition of the basal experimental diets

| Ingredients | Starter (0-14 d) % | Grower (15-21 d) % | Finisher (22-35 d) % |
|---|---|---|---|
| Corn | 57.59 | 59.20 | 62.30 |
| Wheat Flour | 1.00 | 1.00 | 1.00 |
| Soybean Meal (46% CP) | 30.00 | 28.00 | 24.50 |
| Poultry Meal | 5.00 | 5.00 | 5.00 |
| Poultry Fat | 2.10 | 2.86 | 3.52 |
| Limestone (36% Ca) | 1.05 | 1.02 | 0.98 |
| Dicalcium Phosphate (18% P) | 1.76 | 1.52 | 1.42 |
| Salt | 0.35 | 0.32 | 0.29 |
| Sodium Bicarbonate | 0.16 | 0.14 | 0.11 |
| L-Lysine HCL (78%) | 0.23 | 0.22 | 0.21 |
| DL-Methionine (99%) | 0.36 | 0.33 | 0.29 |

TABLE 9.2-continued

Composition of the basal experimental diets

| Ingredients | Starter (0-14 d) % | Grower (15-21 d) % | Finisher (22-35 d) % |
|---|---|---|---|
| L-Threonine (98%) | 0.05 | 0.04 | 0.03 |
| Selenium premix | 0.05 | 0.05 | 0.05 |
| Vitamin Mix | 0.15 | 0.15 | 0.15 |
| Mineral Mix | 0.15 | 0.15 | 0.15 |
| Calculated Nutritional Content | | | |
| ME (kcal/kg) | 2968 | 3032 | 3096 |
| Crude Protein (%) | 23.3 | 22.4 | 20.78 |
| Lysine (%) | 1.35 | 1.29 | 1.18 |
| Methionine (%) | 0.69 | 0.65 | 0.59 |
| Met + Cys (%) | 1.05 | 1.00 | 0.92 |
| Threonine (%) | 0.86 | 0.81 | 0.75 |
| Calcium (%) | 1.03 | 0.96 | 0.91 |
| Phosphorus Avail. (%) | 0.46 | 0.41 | 0.39 |

[1] Vitamin mix will provide the following (per kg of diet): vitamin A, 13 227 513 IU; vitamin D3, 3 968 254 IU; vitamin E, 66 138 IU; vitamin $B_{12}$, 40 mg; biotin, 254 mg; menadione, 3 968 mg; thiamine, 3 968 mg; riboflavin, 13 228 mg; d-Pantothenic Acid, 22 046 mg; pyridoxine, 7 937 mg; niacin, 110 229 mg; folic acid, 2 205 mg; Selenium Premix: selenium, 600 ppm + calcium, 36%
[2] Trace mineral mix provided the following (per kg of diet): calcium, Min: 15.7% and Max: 18.7%; manganese (Mn), 6.0%; zinc (Zn), 6.0%; iron (Fe), 4.0%; copper (Cu), 5000 ppm; iodine (I), 1250 ppm; cobalt (Co), 500 ppm Experimental Results The results obtained on performance parameters for the whole experimental period are shown in Table 9.3.

TABLE 9.3

Effect of dietary supplementation of the strains DSM 29870, DSM 29871 and DSM 29872 on broiler performance

| Parameters[4] | Control[1] | DSM 29870[2] supplemented group | DSM 29871[2] supplemented group | DSM 29872[2] supplemented group | GalliPro Max[3] supplemented group |
|---|---|---|---|---|---|
| FI (g/bird) | 3573a | 3542a | 3606a | 3515a | 3541a |
| Relative to the control | — | −0.9% | +0.9% | −1.0% | −0.9% |
| BWG (g/bird) | 2361a | 2416b | 2401ab | 2424b | 2398ab |
| Relative to the control | — | +2.3% | +1.7% | +2.6% | +1.5% |
| FCR | 1.513a | 1.467b | 1.501bc | 1.451a | 1.477ab |
| Relative to the control | — | −3.6% | −0.8% | −4.2% | −2.4% |
| Mortality (%) | 15.6ab | 7.8a | 11.7ab | 19.4b | 10.0a |

[1] Group fed with the basal diet
[2] DSM 29870/29871/29872 supplemented group fed with the basal diet including strain DSM 29870/29871/29872 at $5 \cdot 10^8$ CFU/kg of feed.
[3] GalliPro Max supplemented group fed with the basal diet including GalliPro Max at $8 \cdot 10^8$ CFU/kg of feed.
[4] Means from 12 replicates of 15 birds per pen for each group. Raw data (n = 36) were analyzed using variance analysis with block (n = 12) and treatments (n = 3) as fixed effect.
a, b, cValues with different superscripts are significantly ($P < 0.05$) different from each other Also in this experiment, the administration of the strains DSM 29870, DSM 29871, DSM 29872 and GalliPro Max did not significantly reduce the feed intake, but improved the body weight gain by 2.3%, 1.7%, 2.6% and 1.5%, respectively. Therefore, difference relatively to control was significant for DSM 29870 and DSM 29872.

The strains DSM 29870 and DSM 29872 improved significantly the feed conversion ratio by 3.6% and 4.2%, respectively. DSM 29871 and GalliPro Max also improved (slightly for DSM 29871) the feed conversion ratio in this experiment, but not significantly.

The strain DSM 29870 allowed a decrease of the mortality level in a numerically higher manner than GalliPro Max.

Example 10: Third Performance Trial with Broiler Chickens (051)

Material and Methods

A total of 1080 one day-old male broiler chickens Ross PM3 were individually weighed (body weight 42±3.5 g) and allocated in floor pens (18 birds/pens). Pens were used in factorial and completely randomized design with 12 pens per treatment (i.e., 216 animals/treatment). The 3 experimental treatments consisted in (Table 10.1): T1, negative control basal diets; T2, basal diets containing the strain DSM 29870 (included at $5 \cdot 10^8$ CFU/kg of feed, from d1 to d35); T3, basal diets containing the strain DSM 29871 (included at $5 \cdot 10^8$ CFU/kg of feed, from d1 to d35); T4 basal diets containing the strain DSM 29872 (included at $5 \cdot 10^8$ CFU/kg of feed, from d1 to d35); T5, basal diet containing a marketed probiotic, GalliPro Max (included at the commercial dose, $8 \cdot 10^8$ CFU/kg of feed, from d1 to d35).

Basal diets consisted in 3 phases feeding program: starter phase (from 1 to day 21) and grower phase (from 22 to day 35). Every phases were formulated to meet or exceed animal requirement and agree with standard commercial EU corn-soybean meal-based broiler diets. The dietary and raw material composition of these diets is given in Table 10.2. All experimental diets included vitamin and mineral pre-mixes, but did not contain any coccidiostat, NSPase, phytase or growth promoting substance. Feed and water were available ad libitum throughout the trial.

TABLE 10.1

Experimental treatments

| Treatments | |
|---|---|
| T1 | Control |
| T2 | T1 + DSM 29870 |
| T3 | T1 + DSM 29871 |
| T4 | T1 + DSM 29872 |
| T5 | T1 + GalliPro Max |

TABLE 10.2

Composition of the basal experimental diets

| Ingredients | Starter (0-21 d) % | Grower (22-35 d) % |
|---|---|---|
| Maize | 51.68 | 55.58 |
| Soybean Meal (48% CP) | 39.03 | 34.55 |
| Soybean oil | 4.27 | 5.18 |
| DL-Methionine | 0.22 | 0.17 |
| Calcium carbonate | 1.05 | 1.05 |
| Dicalcium Phosphate | 1.78 | 1.5 |
| Salt | 0.37 | 0.37 |
| Wheat middlings | 1.00 | 1.00 |
| Premix[1] | 0.6 | 0.6 |
| Calculated Nutritional Content | | |
| ME (kcal/kg) | 3000 | 3100 |
| Crude Protein (%) | 22.25 | 20.5 |
| Fat (%) | 6.76 | 7.7 |
| Cellulose (%) | 3.15 | 3 |
| Minerals (%) | 5.74 | 5.3 |
| Lysine (%) | 1.25 | 1.13 |
| Methionine (%) | 0.55 | 0.48 |
| Met + Cys (%) | 0.92 | 0.83 |
| Threonine (%) | 0.87 | 0.8 |
| Calcium (%) | 0.93 | 0.85 |
| Total phosphorus | 0.7 | 0.63 |
| Phosphorus Avail. (%) | 0.38 | 0.33 |

[1]The premix will provide the following (per kg of diet): vitamin A, 12 000 IU; vitamin D3, 3 000 IU;, vitamin E = 300 IU;, vitamin K3, 3 mg; vitamin B, 2 mg; vitamin B2, 8 mg; vitamin B6, 3 mg; vitamin B12, 0.02 mg; folic acid, 1 mg; biotin, 0.2 mg; calcium pantothenate, 15 mg; nicotinic acid, 40 mg; manganese (Mn), 80 mg; zinc (Zn), 60 mg; iodine (I), 1 mg; iron (Fe), 80 mg; copper (Cu), 15 mg; cobalt (Co), 0.4 mg; selenium (Se), 0.2 mg; magnesium (Mg), 5 mg; Etoxyquin, 0.5 mg; BHA, 0.5 mg, citric acid, 5 mg; phosphoric acid, 5 mg.

Experimental Results

The results obtained on performance parameters for the whole experimental period are shown in Table 10.3.

TABLE 10.3

Effect of dietary supplementation of the strains DSM 29870, DSM 29871 and DSM 29872 on broiler performance

| Parameters[4] | Control[1] | DSM 29870[2] supplemented group | DSM 29871[2] supplemented group | DSM 29872[2] supplemented group | GalliPro Max[3] supplemented group |
|---|---|---|---|---|---|
| FI (g/bird) | 3217a | 3295a | 3281a | 3230a | 3246a |
| Relative to the control | — | +2.4% | +2.0% | +0.4% | +0.9% |
| BWG (g/bird) | 2019b | 2149a | 2167a | 2124a | 2103ab |
| Relative to the control | — | +6.5% | +7.3% | +5.2% | +4.2% |
| FCR | 1.598a | 1.534b | 1.513b | 1.521b | 1.544b |
| Relative to the control | — | −4.0% | −5.3% | −4.8% | −3.4% |
| Mortality (%) | 11.1a | 9.7a | 8.3a | 6.5a | 7.4a |

[1]Group fed with the basal diet.

[2]DSM 29870/29871/29872 supplemented group fed with the basal diet including strain DSM 29870/29871/29872 at $5.10^8$ CFU/kg of feed.

[3]GalliPro Max supplemented group fed with the basal diet including GalliPro Max at $8.10^8$ CFU/kg of feed.

[4]Means from 12 replicates of 18 birds per pen for each group. Raw data (n = 36) were analyzed using variance analysis with block (n = 12) and treatments (n = 3) as fixed effect.

a, b, cValues with different superscripts are significantly (P < 0.05) different from each other.

In this experiment, the administration of the strains DSM 29870, DSM 29871, DSM 29872 (as GalliPro Max) had not significant effect on the feed intake, but led to the significant improvement of the body weight gain by 6.5%, 7.3% and 5.2%, respectively. GalliPro Max improved also the body weight gain (+4.2%), but not significantly.

All NZB strains improved significantly the feed conversion ratio by 4.0%, 5.3% and 4.8% (DSM 29870, DSM 29871 and DSM 29872, respectively) as GalliPro Max which reached 3.4% of improvement.

Regarding the mortality level, there were no significant differences between the treatments.

Example 11: Synthesis and Meta-Analysis

The results of the three performance experiments described above are summarized in Table 11.1.

TABLE 11.1

Results of the individual studies

| Trial | Treatments | FI (g/bird) | Relative to the control | BWG (g/bird) | Relative to the control | FCR | Relative to the control |
|---|---|---|---|---|---|---|---|
| 1 | Control | 3245a | – | 1987ab | – | 1.633a | – |
|  | DSM 29870 | 3256a | +0.3% | 2026ab | +2.0% | 1.607b | −1.6% |
|  | DSM 29871 | 3221a | −0.7% | 2002ab | +0.8% | 1.609b | −1.5% |
|  | DSM 29872 | 3263a | +0.6% | 2038a | +2.6% | 1.602b | −2.0% |
|  | GalliPro Max | 3203a | −1.3% | 1973b | −0.7% | 1.624ab | −0.6% |
| 2 | Control | 3573a | – | 2361a | – | 1.513a | – |
|  | DSM 29870 | 3542a | −0.9% | 2416b | +2.3% | 1.467b | −3.6% |
|  | DSM 29871 | 3606a | +0.9% | 2401ab | +1.7% | 1.501bc | −0.8% |
|  | DSM 29872 | 3515a | −1.0% | 2424b | +2.6% | 1.451a | −4.2% |
|  | GalliPro Max | 3541a | −0.9% | 2398ab | +1.5% | 1.477ab | −2.4% |
| 3 | Control | 3217a | – | 2019b | – | 1.598a | – |
|  | DSM 29870 | 3295a | +2.4% | 2149a | +6.5% | 1.534b | −4.0% |
|  | DSM 29871 | 3281a | +2.0% | 2167a | +7.3% | 1.513b | −5.3% |
|  | DSM 29872 | 3230a | +0.4% | 2124a | +5.2% | 1.521b | −4.8% |
|  | GalliPro Max | 3246a | +0.9% | 2103ab | +4.2% | 1.544b | −3.4% | a,b,cValues with different superscripts are significantly (P < 0.05) different from each other.

These trials having a similar experimental design, all the data obtained were pooled and combined in a meta-analysis (after having been tested for homogeneity). This meta-analysis involved 3 980 broilers in 160 replicates (32 replicates and 796 animals for each experimental group). The results are shown in Table 11.

Data (n=160) were subjected to a mixed model ANOVA, using the GLIMMIX procedure of SAS (SAS Institute, 2002-2012) to establish differences between diets. Pen was considered as the experimental unit. The model included diets (n=5) as fixed effect and experiment (n=3) as random effect. Results are reported as least square means. LS means were assumed to be different at P 0.05.

TABLE 11.2 meta-analysis of three experiments showing the effect of dietary supplementation of the strain DSM 29870, DSM 29871 and DSM 29872 on broiler performance

| Parameters[4] | Control[1] | DSM 29870[2] supplemented group | DSM 29871[2] supplemented group | DSM 29872[2] supplemented group | GalliPro Max[3] supplemented group |
|---|---|---|---|---|---|
| FI (g/bird) | 3343a | 3360a | 3361a | 3356a | 3347a |
| Relative to the control | — | +0.5% | +0.5% | +0.4% | +0.1% |
| BWG (g/bird) | 2145b | 2208a | 2202ab | 2211a | 2171ab |
| Relative to the control | — | +2.9% | +2.6% | +3.0% | +1.2% |
| FCR | 1.560a | 1.530b | 1.53bc | 1.52c | 1.550ab |
| Relative to the control | — | −2.4% | −2.2% | −2.7% | −1.1% |

[1]Group fed with the basal diet
[2]DSM 29870/29871/29872 supplemented group fed with the basal diet including strain DSM 29870/29871/29872 at 5.10[8] CFU/kg of feed.
[3]GalliPro Max supplemented group fed with the basal diet including GalliPro Max at 8.10[8] CFU/kg of feed.
[4]Means from 32 observations for each experimental group (796 animals/group).
a, b, cValues with different superscripts are significantly (P < 0.05) different from each other.

This meta-analysis showed that the use of the strain DSM 29870, DSM 29871 or DSM 29872 in a corn/soybean meal-based diet significantly improved in average the body weight gain (+2.9%, +2.6% and +3.0%, respectively) and the feed conversion ratio (−2.4%, −2.2% and −2.7%, respectively) with no effect on the feed intake.

CONCLUSION

In the working examples above, positive effects of strain DSM 29870 have been demonstrated on broiler performances (i.e., body weight gain and feed conversion ratio) fed a corn/soybean meal-based diet.

All the data obtained from the experiments described in the above examples also showed that the effect of strain DSM 29870 on the feed conversion ratio is due to its effect on the body weight. These effects might be associated with either health effect or metabolism improvement.

Strain DSM 29870 showed positive and significant effects on body weight gain and feed conversion ratio in 66% and 100% of the working examples above, respectively.

GalliPro Max showed no significant effect on the body weight gain in any of the working examples above and showed significant and positive effect on feed conversion ratio in one third of the experiments.

In the experiments described in the above examples, the better effect of strain DSM 29870 compared to GalliPro Max on broilers performance has been demonstrated. The effect observed using DSM 29870 were in average twice those observed for GalliPro Max.

Example 12: Determination of Monensin Compatibility

Monensin compatibility of *Bacillus* strains DSM 29869, DSM 29870, DSM 29871, and DSM 29872 was determined using a modified broth micro dilution similar to the method described in the Example 5. Briefly, a single colony of *Bacillus* spp. (from overnight tryptic soy agar plates) was inoculated into Mueller Hinton Broth (MHB) and cultured overnight. Sterile media was the inoculated with the overnight culture and allowed to grow for 4 hours to test bacteria in log growth phase. Cultures were then diluted once more 1:200 into fresh MHB and 90 µL of this inoculated broth was added to the diluted monensin at the indicated concentrations. Prior art strains were also tested for comparison: NN019785, NN062266 (NRRL B-50013), NN062267 (NRRL B-50104), NN062278 (PTA-6507), NN062319 (FERM BP-1096), NN062440, NN062441 (DSM 17236), NN062439.

Strains:

*Bacillus amyloliquefaciens* DSM 29869

*Bacillus subtilis* DSM 29870

*Bacillus subtilis* DSM 29871

*Bacillus amyloliquefaciens* DSM 29872

*Bacillus licheniformis* NN019785

*Bacillus amyloliquefaciens* NN062266 (NRRL B-50013)

*Bacillus subtilis* NN062267 (NRRL B-50104)

*Bacillus subtilis* NN062278 (PTA-6507)

*Bacillus amyloliquefaciens* NN062319 (FERM BP-1096)

*Bacillus subtilis* NN062440

*Bacillus licheniformis* NN062441 (DSM 17236)

*Bacillus amyloliquefaciens* NN062439

Materials:

Monensin sodium salt (Sigma, CAS no. 22373-78-0, solubilized in 96% ethanol)

Mueller Hinton Broth (Becton, Dickinson and Company, 275730)

Tryptic soy agar (Becton, Dickinson and Company, 236920)

Micro titer plates: Costar plate, polypropylene, flat bottom, Corning, 3628

Borosilicate glass tubes: Kimbale, 16×125 mm, 73500-16125

Adhesive gas permeable seals: Thermo Scientific, AB-0718

Preparation of Bacteria:

*Bacillus* spp. were grown overnight on tryptic soy agar plates (40 g/L) at 37° C. Mueller Hinton broth (21 g/L) was dissolved in water and autoclaved in glass tubes containing 5 mL of broth each. A single colony of *Bacillus* spp. (from overnight plates) was inoculated into Mueller Hinton Broth (MHB) and incubated overnight at 37° C. shaking at 200 rpm. A 5 mL glass tube of fresh, sterile media was then inoculated with 25 mL of overnight culture and allowed to grow for 4 hours at 37° C. Cultures were then diluted once more 1:200 into fresh MHB. 90 µL of this inoculated broth was then added to the diluted antibiotic at the indicated concentrations.

Preparation of Assay Plates:

Monensin was diluted into 96% ethanol to a concentration of 800 µg/mL. This solution was then diluted 10-fold into sterile phosphate buffer to a concentration of 80 µg/mL. A two fold dilution series was prepared in MHB down to the concentration 2.5 µg/m L. 10 µl of each dilution and of each antibiotic was pipetted into a micro titer plate. Later, when the antibiotics were mixed with the suspension of bacteria, the samples were diluted 10× (10 µL sample in a total volume of 100 µl). This resulted in the final test range of 0.25-8 µg/ml.

90 µl of the bacterial suspensions were added to the assay plates. The assay plates were then covered with an adhesive glass permeable seal and incubated overnight at 37° C. shaking at 200 rpm. The maximum compatible concentration was determined similar to a MIC analysis as the concentration above that which inhibited 80% of bacteria as detected by the unaided eye.

Results:

A potential challenge of delivering *Bacillus* spp. in feed is the common use of antibiotics as growth promoters in feed. Therefore it is necessary to determine the compatibility of strains with commonly-used feed antibiotics in order to identify any potential conflicts with use as a direct fed microbial. Therefore, the monensin compatibility of *Bacillus* strains DSM 29869, DSM 29870, DSM 29871, and DSM 29872 were determined along with prior art strains. *Bacillus* strains DSM 29869, DSM 29870, DSM 29871, and DSM 29872 indicated a higher level of compatibility with monensin than most of the prior art strains included herein: NN019785, NN062266 (NRRL B-50013), NN062267 (NRRL B-50104), NN062278 (PTA-6507), NN062319 (FERM BP-1096), NN062440, NN062441 (DSM 17236), NN062439.

TABLE 12.1

Monensin compatibility results

| | | Species | Product Name | Monensin (µg/mL) |
|---|---|---|---|---|
| NN062677 | DSM29870 | *Bacillus subtilis* | | 2.7 |
| NN062673 | DSM29871 | *Bacillus subtilis* | | 2.0 |
| NN062683 | DSM29872 | *Bacillus amyloliquefaciens* | | 4.0 |
| NN062676 | DSM29869 | *Bacillus amyloliquefaciens* | | 2.0 |
| NN019785 | | *Bacillus licheniformis* | BioPlus 2B (Chr. Hansen) | 0.8 |
| NN062266 | NRRL B-50013 | *Bacillus amyloliquefaciens* | Eviva Pro (Dupont) | 1.1 |
| NN062267 | NRRL B-50104 | *Bacillus subtilis* | Eviva Pro (Dupont) | 1.1 |
| NN062278 | PTA-6507 | *Bacillus subtilis* | Eviva Pro (Dupont) | 1.4 |
| NN062319 | FERM BP-1096 | *Bacillus amyloliquefaciens* | Calsporin (Calpis) | 2.2 |
| NN062440 | | *Bacillus subtilis* | GalliPro Max (Chr. Hansen) | 0.4 |
| NN062441 | DSM17236 | *Bacillus licheniformis* | GalliPro Tect (Chr. Hansen) | 0.9 |
| NN062439 | | *Bacillus amyloliquefaciens* | Clostat (Kernin) | 2.1 |

What is claimed is:

1. A method comprising administering *Bacillus subtilis* DSM 29870 to an animal.

2. The method of claim 1, wherein said administering comprises administering spores of *Bacillus subtilis* DSM 29870 to said animal.

3. The method of claim 1, wherein *Bacillus subtilis* DSM 29870 is fed to said animal.

4. The method of claim 2, wherein *Bacillus subtilis* DSM 29870 is fed to said animal as part of an animal feed composition.

5. The method of claim 2, wherein *Bacillus subtilis* DSM 29870 is fed to said animal as part of a composition comprising between $1 \times 10^4$ and $1 \times 10^{18}$ colony forming units of *Bacillus subtilis* DSM 29870 per kilogram of said composition.

6. The method of claim 2, wherein *Bacillus subtilis* DSM 29870 is fed to said animal as part of a composition comprising one or more enzymes.

7. The method of claim 2, wherein *Bacillus subtilis* DSM 29870 is fed to said animal as part of a composition comprising one or more feed ingredients.

8. The method of claim 2, wherein *Bacillus subtilis* DSM 29870 is fed to said animal as part of a composition comprising one or more vitamins.

9. The method of claim 2, wherein *Bacillus subtilis* DSM 29870 is fed to said animal as part of a composition comprising one or more flowability agents.

10. The method of claim 2, wherein *Bacillus subtilis* DSM 29870 is fed to said animal as part of a composition comprising one or more additional microbes.

11. The method of claim 2, wherein *Bacillus subtilis* DSM 29870 is fed to said animal as part of a composition comprising extruded animal feed pellets.

12. The method of claim 2, wherein said animal is mono-gastric.

13. The method of claim 2, wherein said animal is a poultry animal.

14. The method of claim 2, wherein said animal is a swine animal.

15. The method of claim 2, wherein *Bacillus subtilis* DSM 29870 is administered to said animal in an amount sufficient to improve one or more performance parameters of said animal, as compared to that of a control animal that was not administered *Bacillus subtilis* DSM 29870.

16. The method of claim 2, wherein *Bacillus subtilis* 298 is administered to said animal in an amount sufficient to improve body weight gain of said animal, as compared to that of a control animal that was not administered *Bacillus subtilis* DSM 29870.

17. The method of claim 2, wherein *Bacillus subtilis* DSM 29870 is administered to said animal in an amount sufficient to improve a feed conversion ratio of said animal, as compared to that of a control animal that was not administered *Bacillus subtilis* DSM 29870.

18. The method of claim 2, wherein *Bacillus subtilis* DSM 29870 is administered to said animal in an amount sufficient to improve the feed efficiency of said animal, as compared to that of a control animal that was not administered *Bacillus subtilis* DSM 29870.

19. The method of claim 2, wherein *Bacillus subtilis* DSM 29870 is administered to said animal in an amount sufficient to reduce one or more symptoms of *Clostridium perfringens* infection.

20. The method of claim 2, wherein *Bacillus subtilis* DSM 29870 is administered to said animal in an amount sufficient to reduce one or more symptoms of necrotic enteritis.

* * * * *

SEQUENCE LISTING

<160> NUMBER OF SEQ ID NOS: 13

<210> SEQ ID NO 1
<211> LENGTH: 1507
<212> TYPE: DNA
<213> ORGANISM: Bacillus amyloliquefaciens

<400> SEQUENCE: 1

```
gacgaacgct ggcggcgtgc ctaatacatg caagtcgagc ggacagatgg gagcttgctc      60
cctgatgtta gcggcggacg ggtgagtaac acgtgggtaa cctgcctgta agactgggat     120
aactccggga aaccggggct aataccggat ggttgtttga accgcatggt tcagacataa     180
aaggtggctt cggctaccac ttacagatgg acccgcggcg cattagctag ttggtgaggt     240
aacggctcac caaggcaacg atgcgtagcc gacctgagag ggtgatcggc cacactggga     300
ctgagacacg gcccagactc ctacgggagg cagcagtagg gaatcttccg caatggacga     360
aagtctgacg gagcaacgcc gcgtgagtga tgaaggtttt cggatcgtaa agctctgttg     420
ttagggaaga acaagtgccg ttcaaatagg gcggcacctt gacggtacct aaccagaaag     480
ccacggctaa ctacgtgcca gcagccgcgg taatacgtag gtggcaagcg ttgtccggaa     540
ttattgggcg taaagggctc gcaggcggtt tcttaagtct gatgtgaaag cccccggctc     600
aaccggggag ggtcattgga aactgggaaa cttgagtgca gaagaggaga gtggaattcc     660
acgtgtagcg gtgaaatgcg tagagatgtg gaggaacacc agtggcgaag gcgactctct     720
ggtctgtaac tgacgctgag gagcgaaagc gtggggagcg aacaggatta gataccctgg     780
tagtccacgc cgtaaacgat gagtgctaag tgttaggggg tttccgcccc ttagtgctgc     840
agctaacgca ttaagcactc cgcctgggga gtacggtcgc aagactgaaa ctcaaaggaa     900
ttgacggggg cccgcacaag cggtggagca tgtggtttaa ttcgaagcaa cgcgaagaac     960
cttaccaggt cttgacatcc tctgacaatc ctagagatag gacgtcccct cggggggcag    1020
agtgacaggt ggtgcatggt tgtcgtcagc tcgtgtcgtg agatgttggg ttaagtcccg    1080
caacgagcgc aacccttgat cttagttgcc agcattcagt tgggcactct aaggtgactg    1140
ccggtgacaa accggaggaa ggtggggatg acgtcaaatc atcatgcccc ttatgacctg    1200
ggctacacac gtgctacaat gggcagaaca aagggcagcg aaaccgcgag gttaagccaa    1260
tcccacaaat ctgttctcag ttcggatcgc agtctgcaac tcgactgcgt gaagctggaa    1320
```

```
tcgctagtaa tcgcggatca gcatgccgcg gtgaatacgt tcccgggcct tgtacacacc   1380
gcccgtcaca ccacgagagt ttgtaacacc cgaagtcggt gaggtaacct tttaggagcc   1440
agccgccgaa ggtgggacag atgattgggg tgaagtcgta acaaggtagc cgtatcggaa   1500
ggtgcgg                                                              1507

<210> SEQ ID NO 2
<211> LENGTH: 1507
<212> TYPE: DNA
<213> ORGANISM: Bacillus subtilis

<400> SEQUENCE: 2
gacgaacgct ggcggcgtgc ctaatacatg caagtcgagc ggacagatgg gagcttgctc     60
cctgatgtta gcggcggacg ggtgagtaac acgtgggtaa cctgcctgta agactgggat    120
aactccggga aaccggggct aataccggat gcttgtttga accgcatggt tcaaacataa    180
aaggtggctt cggctaccac ttacagatgg acccgcggcg cattagctag ttggtgaggt    240
aacggctcac caaggcaacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgagtga tgaaggtttt cggatcgtaa agctctgttg    420
ttagggaaga acaagtaccg ttcgaatagg gcggtacctt gacggtacct aaccagaaag    480
ccacggctaa ctacgtgcca gcagccgcgg taatacgtag gtggcaagcg ttgtccggaa    540
ttattgggcg taaagggctc gcaggcggtt tcttaagtct gatgtgaaag ccccggctc     600 aaccggggag ggtcattgga aactgggaa cttgagtgca agaggaga gtggaattcc       660 acgtgtagcg gtgaaatgcg tagagatgtg gaggaacacc agtggcgaag gcgactctct    720
ggtctgtaac tgacgctgag gagcgaaagc gtggggagcg aacaggatta gataccctgg    780
tagtccacgc cgtaaacgat gagtgctaag tgttagggggg tttccgcccc ttagtgctgc    840
agctaacgca ttaagcactc cgcctgggga gtacggtcgc aagactgaaa ctcaaaggaa    900
ttgacggggg cccgcacaag cggtggagca tgtggtttaa ttcgaagcaa cgcgaagaac    960
cttaccaggt cttgacatcc tctgacaatc ctagagatag gacgtcccct tcggggggcag  1020 agtgacaggt ggtgcatggt tgtcgtcagc tcgtgtcgtg agatgttggg ttaagtcccg   1080
caacgagcgc aacccttgat cttagttgcc agcattcagt tgggcactct aaggtgactg   1140
ccggtgacaa accggaggaa ggtggggatg acgtcaaatc atcatgcccc ttatgacctg   1200
ggctacacac gtgctacaat ggacagaaca aagggcagcg aaaccgcgag gttaagccaa   1260
tcccacaaat ctgttctcag ttcggatcgc agtctgcaac tcgactgcgt gaagctggaa   1320
tcgctagtaa tcgcggatca gcatgccgcg gtgaatacgt tcccgggcct tgtacacacc   1380
gcccgtcaca ccacgagagt ttgtaacacc cgaagtcggt gaggtaacct tttaggagcc   1440
agccgccgaa ggtgggacag atgattgggg tgaagtcgta acaaggtagc cgtatcggaa   1500
ggtgcgg                                                              1507

<210> SEQ ID NO 3
<211> LENGTH: 1507
<212> TYPE: DNA
<213> ORGANISM: Bacillus subtilis

<400> SEQUENCE: 3
gacgaacgct ggcggcgtgc ctaatacatg caagtcgagc ggacagatgg gagcttgctc     60
```

```
cctgatgtta gcggcggacg ggtgagtaac acgtgggtaa cctgcctgta agactgggat      120
aactccggga aaccggggct aataccggat ggttgtttga accgcatggt tcaaacataa      180
aaggtggctt cggctaccac ttacagatgg acccgcggcg cattagctag ttggtgaggt      240
aacggctcac caaggcaacg atgcgtagcc gacctgagag ggtgatcggc cacactggga      300
ctgagacacg gcccagactc ctacgggagg cagcagtagg gaatcttccg caatggacga      360
aagtctgacg gagcaacgcc gcgtgagtga tgaaggtttt cggatcgtaa agctctgttg      420
ttagggaaga acaagtaccg ttcgaatagg gcggtacctt gacggtacct aaccagaaag      480
ccacggctaa ctacgtgcca gcagccgcgg taatacgtag gtggcaagcg ttgtccggaa      540
ttattgggcg taaagggctc gcaggcggtt tcttaagtct gatgtgaaag ccccggctc       600 aaccggggag ggtcattgga aactgggaa cttgagtgca gaagaggaga gtggaattcc      660
acgtgtagcg gtgaaatgcg tagagatgtg gaggaacacc agtggcgaag gcgactctct      720
ggtctgtaac tgacgctgag gagcgaaagc gtggggagcg aacaggatta gataccctgg      780
tagtccacgc cgtaaacgat gagtgctaag tgttaggggg tttccgcccc ttagtgctgc      840
agctaacgca ttaagcactc cgcctgggga gtacggtcgc aagactgaaa ctcaaaggaa      900
ttgacggggg cccgcacaag cggtggagca tgtggtttaa ttcgaagcaa cgcgaagaac      960
cttaccaggt cttgacatcc tctgacaatc ctagagatag gacgtcccct tcggggggcag     1020 agtgacaggt ggtgcatggt tgtcgtcagc tcgtgtcgtg agatgttggg ttaagtcccg     1080
caacgagcgc aacccttgat cttagttgcc agcattcagt tgggcactct aaggtgactg     1140
ccggtgacaa accggaggaa ggtggggatg acgtcaaatc atcatgcccc ttatgacctg     1200
ggctacacac gtgctacaat ggacagaaca aagggcagcg aaaccgcgag gttaagccaa     1260
tcccacaaat ctgttctcag ttcggatcgc agtctgcaac tcgactgcgt gaagctggaa     1320
tcgctagtaa tcgcggatca gcatgccgcg gtgaatacgt tcccgggcct tgtacacacc     1380
gcccgtcaca ccacgagagt ttgtaacacc cgaagtcggt gaggtaacct tttaggagcc     1440
agccgccgaa ggtgggacag atgattgggg tgaagtcgta acaaggtagc cgtatcggaa     1500
ggtgcgg                                                                1507
```

<210> SEQ ID NO 4
<211> LENGTH: 1507
<212> TYPE: DNA
<213> ORGANISM: Bacillus amyloliquefaciens

<400> SEQUENCE: 4

```
gacgaacgct ggcggcgtgc ctaatacatg caagtcgagc ggacagatgg gagcttgctc       60
cctgatgtta gcggcggacg ggtgagtaac acgtgggtaa cctgcctgta agactgggat      120
aactccggga aaccggggct aataccggat ggttgtctga accgcatggt tcagacataa      180
aaggtggctt cggctaccac ttacagatgg acccgcggcg cattagctag ttggtgaggt      240
aacggctcac caaggcgacg atgcgtagcc gacctgagag ggtgatcggc cacactggga      300
ctgagacacg gcccagactc ctacgggagg cagcagtagg gaatcttccg caatggacga      360
aagtctgacg gagcaacgcc gcgtgagtga tgaaggtttt cggatcgtaa agctctgttg      420
ttagggaaga acaagtgccg ttcaaatagg gcggcacctt gacggtacct aaccagaaag      480
ccacggctaa ctacgtgcca gcagccgcgg taatacgtag gtggcaagcg ttgtccggaa      540
ttattgggcg taaagggctc gcaggcggtt tcttaagtct gatgtgaaag ccccggctc       600 aaccggggag ggtcattgga aactgggaa cttgagtgca gaagaggaga gtggaattcc      660
```

```
acgtgtagcg gtgaaatgcg tagagatgtg gaggaacacc agtggcgaag gcgactctct    720
ggtctgtaac tgacgctgag gagcgaaagc gtggggagcg aacaggatta gataccctgg    780
tagtccacgc cgtaaacgat gagtgctaag tgttaggggg tttccgcccc ttagtgctgc    840
agctaacgca ttaagcactc cgcctgggga gtacggtcgc aagactgaaa ctcaaaggaa    900
ttgacggggg cccgcacaag cggtggagca tgtggtttaa ttcgaagcaa cgcgaagaac    960
cttaccaggt cttgacatcc tctgacaatc ctagagatag gacgtcccct tcggggcag   1020 agtgacaggt ggtgcatggt tgtcgtcagc tcgtgtcgtg agatgttggg ttaagtcccg   1080
caacgagcgc aacccttgat cttagttgcc agcattcagt tgggcactct aaggtgactg   1140
ccggtgacaa accggaggaa ggtggggatg acgtcaaatc atcatgcccc ttatgacctg   1200
ggctacacac gtgctacaat ggacagaaca aagggcagcg aaaccgcgag gttaagccaa   1260
tcccacaaat ctgttctcag ttcggatcgc agtctgcaac tcgactgcgt gaagctggaa   1320
tcgctagtaa tcgcggatca gcatgccgcg gtgaatacgt tcccgggcct tgtacacacc   1380
gcccgtcaca ccacgagagt ttgtaacacc cgaagtcggt gaggtaacct ttaaggagcc   1440
agccgccgaa ggtgggacag atgattgggg tgaagtcgta acaaggtagc cgtatcggaa   1500
ggtgcgg                                                              1507

<210> SEQ ID NO 5
<211> LENGTH: 1472
<212> TYPE: DNA
<213> ORGANISM: Bacillus vallismortis

<400> SEQUENCE: 5
gacgaacgct ggcggcgtgc ctaatacatg caagtcgagc ggacagatgg gagcttgctc     60
cctgatgtta gcggcggacg ggtgagtaac acgtgggtaa cctgcctgta agactgggat    120
aactccggga aaccggggct aataccggat gcttgtttga accgcatggt tcagacataa    180
aaggtggctt cggctaccac ttacagatgg acccgcggcg cattagctag ttggtgaggt    240
aacggctcac caaggcgacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgagtga tgaaggtttt cggatcgtaa agctctgttg    420
ttagggaaga acaagtgccg ttcaaatagg gcggcacctt gacggtacct aaccagaaag    480
ccacggctaa ctacgtgcca gcagccgcgg taatacgtag gtggcaagcg ttgtccggaa    540
ttattgggcg taaagggctc gcaggcggtt cttaagtct gatgtgaaag cccccggctc    600
aaccggggag ggtcattgga aactgggaa cttgagtgca gaagaggaga gtggaattcc    660
acgtgtagcg gtgaaatgcg tagagatgtg gaggaacacc agtggcgaag gcgactctct    720
ggtctgtaac tgacgctgag gagcgaaagc gtggggagcg aacaggatta gataccctgg    780
tagtccacgc cgtaaacgat gagtgctaag tgttaggggg tttccgcccc ttagtgctgc    840
agctaacgca ttaagcactc cgcctgggga gtacggtcgc aagactgaaa ctcaaaggaa    900
ttgacggggg cccgcacaag cggtggagca tgtggtttaa ttcgaagcaa cgcgaagaac    960
cttaccaggt cttgacatcc tctgacaatc ctagagatag gacgtcccct tcggggcag   1020 agtgacaggt ggtgcatggt tgtcgtcagc tcgtgtcgtg agatgttggg ttaagtcccg   1080
caacgagcgc aacccttgat cttagttgcc agcattcagt tgggcactct aaggtgactg   1140
ccggtgacaa accggaggaa ggtggggatg acgtcaaatc atcatgcccc ttatgacctg   1200
```

| | |
|---|---|
| ggctacacac gtgctacaat gggcagaaca aagggcagcg aaaccgcgag gttaagccaa | 1260 |
| tcccacaaat ctgttctcag ttcggatcgc agtctgcaac tcgactgcgt gaagctggaa | 1320 |
| tcgctagtaa tcgcggatca gcatgccgcg gtgaatacgt tcccgggcct tgtacacacc | 1380 |
| gcccgtcaca ccacgagagt ttgtaacacc cgaagtcggt gaggtaacct ttttggagcc | 1440 |
| agccgccgaa ggtgggacag atgattgggg tg | 1472 |

<210> SEQ ID NO 6
<211> LENGTH: 1507
<212> TYPE: DNA
<213> ORGANISM: Bacillus subtilis

<400> SEQUENCE: 6

| | |
|---|---|
| gacgaacgct ggcggcgtgc ctaatacatg caagtcgagc ggacagatgg gagcttgctc | 60 |
| cctgatgtta gcggcggacg ggtgagtaac acgtgggtaa cctgcctgta agactgggat | 120 |
| aactccggga aaccggggct aataccggat ggttgtttga accgcatggt tcaaacataa | 180 |
| aaggtggctt cggctaccac ttacagatgg acccgcggcg cattagctag ttggtgaggt | 240 |
| aacggctcac caaggcaacg atgcgtagcc gacctgagag ggtgatcggc cacactggga | 300 |
| ctgagacacg gcccagactc ctacgggagg cagcagtagg gaatcttccg caatggacga | 360 |
| aagtctgacg gagcaacgcc gcgtgagtga tgaaggtttt cggatcgtaa agctctgttg | 420 |
| ttagggaaga acaagtaccg ttcgaatagg gcggtacctt gacggtacct aaccagaaag | 480 |
| ccacggctaa ctacgtgcca gcagccgcgg taatacgtag gtggcaagcg ttgtccggaa | 540 |
| ttattgggcg taaagggctc gcaggcggtt tcttaagtct gatgtgaaag ccccggctc | 600 |
| aaccggggag ggtcattgga aactgggaa cttgagtgca gaagaggaga gtggaattcc | 660 |
| acgtgtagcg gtgaaatgcg tagagatgtg gaggaacacc agtggcgaag gcgactctct | 720 |
| ggtctgtaac tgacgctgag gagcgaaagc gtggggagcg aacaggatta gataccctgg | 780 |
| tagtccacgc cgtaaacgat gagtgctaag tgttaggggg tttccgcccc ttagtgctgc | 840 |
| agctaacgca ttaagcactc cgcctgggga gtacggtcgc aagactgaaa ctcaaaggaa | 900 |
| ttgacggggg cccgcacaag cggtggagca tgtggtttaa ttcgaagcaa cgcgaagaac | 960 |
| cttaccaggt cttgacatcc tctgacaatc ctagagatag gacgtcccct cgggggcag | 1020 |
| agtgacaggt ggtgcatggt tgtcgtcagc tcgtgtcgtg agatgttggg ttaagtcccg | 1080 |
| caacgagcgc aacccttgat cttagttgcc agcattcagt tgggcactct aaggtgactg | 1140 |
| ccggtgacaa accggaggaa ggtggggatg acgtcaaatc atcatgcccc ttatgacctg | 1200 |
| ggctacacac gtgctacaat ggacagaaca aagggcagcg aaaccgcgag gttaagccaa | 1260 |
| tcccacaaat ctgttctcag ttcggatcgc agtctgcaac tcgactgcgt gaagctggaa | 1320 |
| tcgctagtaa tcgcggatca gcatgccgcg gtgaatacgt tcccgggcct tgtacacacc | 1380 |
| gcccgtcaca ccacgagagt ttgtaacacc cgaagtcggt gaggtaacct tttaggagcc | 1440 |
| agccgccgaa ggtgggacag atgattgggg tgaagtcgta acaaggtagc cgtatcggaa | 1500 |
| ggtgcgg | 1507 |

<210> SEQ ID NO 7
<211> LENGTH: 1472
<212> TYPE: DNA
<213> ORGANISM: Bacillus amyloliquefaciens

<400> SEQUENCE: 7

| | |
|---|---|
| gacgaacgct ggcggcgtgc ctaatacatg caagtcgagc ggacagatgg gagcttgctc | 60 |

```
cctgatgtta gcggcggacg ggtgagtaac acgtgggtaa cctgcctgta agactgggat    120
aactccggga aaccggggct aataccggat gcttgtttga accgcatggt tcagacataa    180
aaggtggctt cggctaccac ttacagatgg acccgcggcg cattagctag ttggtgaggt    240
aacggctcac caaggcgacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgagtga tgaaggtttt cggatcgtaa agctctgttg    420
ttagggaaga acaagtgccg ttcaaatagg gcggcacctt gacggtacct aaccagaaag    480
ccacggctaa ctacgtgcca gcagccgcgg taatacgtag gtggcaagcg ttgtccggaa    540
ttattgggcg taaagggctc gcaggcggtt tcttaagtct gatgtgaaag ccccgggctc    600
aaccggggag ggtcattgga aactgggaa cttgagtgca gaagaggaga gtggaattcc    660
acgtgtagcg gtgaaatgcg tagagatgtg gaggaacacc agtggcgaag gcgactctct    720
ggtctgtaac tgacgctgag gagcgaaagc gtggggagcg aacaggatta gataccctgg    780
tagtccacgc cgtaaacgat gagtgctaag tgttaggggg tttccgcccc ttagtgctgc    840
agctaacgca ttaagcactc cgcctgggga gtacggtcgc aagactgaaa ctcaaaggaa    900
ttgacggggg cccgcacaag cggtggagca tgtggtttaa ttcgaagcaa cgcgaagaac    960
cttaccaggt cttgacatcc tctgacaatc ctagagatag gacgtcccct tcggggcag     1020 agtgacaggt ggtgcatggt tgtcgtcagc tcgtgtcgtg agatgttggg ttaagtcccg    1080
caacgagcgc aacccttgat cttagttgcc agcattcagt tgggcactct aaggtgactg    1140
ccggtgacaa accggaggaa ggtggggatg acgtcaaatc atcatgcccc ttatgacctg    1200
ggctacacac gtgctacaat gggcagaaca aagggcagcg aaaccgcgag gttaagccaa    1260
tcccacaaat ctgttctcag ttcggatcgc agtctgcaac tcgactgcgt gaagctggaa    1320
tcgctagtaa tcgcggatca gcatgccgcg gtgaatacgt tcccgggcct tgtacacacc    1380
gcccgtcaca ccacgagagt ttgtaacacc cgaagtcggt gaggtaacct ttttggagcc    1440
agccgccgaa ggtgggacag atgattgggg tg                                  1472
```

```
<210> SEQ ID NO 8
<211> LENGTH: 19
<212> TYPE: DNA
<213> ORGANISM: Artificial
<220> FEATURE:
<223> OTHER INFORMATION: PCR primer

<400> SEQUENCE: 8
gagtttgatc ctggctcag                                                  19

<210> SEQ ID NO 9
<211> LENGTH: 20
<212> TYPE: DNA
<213> ORGANISM: Artificial
<220> FEATURE:
<223> OTHER INFORMATION: PCR primer

<400> SEQUENCE: 9
agaaaggagg tgatccagcc                                                 20

<210> SEQ ID NO 10
<211> LENGTH: 21
<212> TYPE: DNA
<213> ORGANISM: Artificial
<220> FEATURE:
```

```
<223> OTHER INFORMATION: PCR Primer

<400> SEQUENCE: 10
atctaatcct gtttgctccc c                                      21

<210> SEQ ID NO 11
<211> LENGTH: 15
<212> TYPE: DNA
<213> ORGANISM: Artificial
<220> FEATURE:
<223> OTHER INFORMATION: PCR primer

<400> SEQUENCE: 11
tacgggaggc agcag                                             15

<210> SEQ ID NO 12
<211> LENGTH: 17
<212> TYPE: DNA
<213> ORGANISM: Artificial
<220> FEATURE:
<223> OTHER INFORMATION: PCR Primer

<400> SEQUENCE: 12
cggtgtgtrc aaggccc                                           17

<210> SEQ ID NO 13
<211> LENGTH: 16
<212> TYPE: DNA
<213> ORGANISM: Artificial
<220> FEATURE:
<223> OTHER INFORMATION: PCR Primer

<400> SEQUENCE: 13
caacgagcgc aaccct                                            16
```

UNITED STATES PATENT AND TRADEMARK OFFICE
CERTIFICATE OF CORRECTION

| | |
|---|---|
| PATENT NO. | : 11,801,272 B2 |
| APPLICATION NO. | : 17/500606 |
| DATED | : October 31, 2023 |
| INVENTOR(S) | : Lewis et al. |

It is certified that error appears in the above-identified patent and that said Letters Patent is hereby corrected as shown below:

In the Claims

Claim 16 (Column 62, Lines 53-57) should read as follows:
16. The method of claim 2, wherein *Bacillus subtilis* DSM 29870 is administered to said animal in an amount sufficient to improve body weight gain of said animal, as compared to that of a control animal that was not administered *Bacillus subtilis* DSM 29870.

Signed and Sealed this
Ninth Day of January, 2024

Katherine Kelly Vidal
*Director of the United States Patent and Trademark Office*